(12) United States Patent
Avendi et al.

(10) Patent No.: US 12,171,592 B2
(45) Date of Patent: Dec. 24, 2024

(54) SYSTEM AND METHOD FOR IDENTIFICATION, LABELING, AND TRACKING OF A MEDICAL INSTRUMENT

(71) Applicant: Avent, Inc., Alpharetta, GA (US)

(72) Inventors: Michael R. Avendi, Irvine, CA (US); Joost L. Mulders, Costa Mesa, CA (US)

(73) Assignee: Avent, Inc., Alpharetta, GA (US)

( * ) Notice: Subject to any disclaimer, the term of this patent is extended or adjusted under 35 U.S.C. 154(b) by 681 days.

(21) Appl. No.: 16/556,461

(22) Filed: Aug. 30, 2019

(65) Prior Publication Data

US 2021/0059758 A1 Mar. 4, 2021

(51) Int. Cl.
*A61B 6/03* (2006.01)
*A61B 5/06* (2006.01)
(Continued)

(52) U.S. Cl.
CPC .............. *A61B 6/032* (2013.01); *A61B 90/37* (2016.02); *G06N 3/084* (2013.01); *G06T 7/0012* (2013.01);
(Continued)

(58) Field of Classification Search
CPC .......... A61B 8/0841; A61B 2034/2065; A61B 34/20; G06V 2201/032; G06V 2201/034;
(Continued)

(56) References Cited

U.S. PATENT DOCUMENTS 7,876,934 B2   1/2011   Gergescu et al.
8,073,220 B2   12/2011  Khamene et al.
(Continued)

FOREIGN PATENT DOCUMENTS

JP   2005199403 A   7/2005
JP   2008017997 A   1/2008
(Continued)

OTHER PUBLICATIONS

Dai et al., "Instance-aware Semantic Segmentation via Multi-task Network Cascades", 2016 IEEE Conference on Computer Vision and Pattern Recognition, Jun. 27, 2016, pp. 3150-3158.
(Continued)

*Primary Examiner* — Colin T. Sakamoto
*Assistant Examiner* — Tommy T Ly
(74) *Attorney, Agent, or Firm* — Meunier Carlin & Curfman LLC

(57) ABSTRACT

The present invention is directed to a computing system and method for the real-time automatic identification and tracking of a medical instrument and optionally the identification of at least one anatomical object in an image generated by an imaging system. The method includes generating the image via the imaging system and providing the image to a processor of a computing system. Further, the method includes developing and training at least one machine-learned model to automatically identify or locate the medical instrument and optionally at least one machine-learned model to identify or locate the anatomical object and the surrounding tissue in the image. Moreover, the method includes automatically labeling the identified medical instrument and optionally the identified anatomical object and surrounding tissue on the image. Further, the method also includes displaying the labeled image to a user in real-time.

13 Claims, 17 Drawing Sheets

(51) Int. Cl.
*A61B 6/12* (2006.01)
*A61B 8/00* (2006.01)
*A61B 8/08* (2006.01)
*A61B 34/20* (2016.01)
*A61B 90/00* (2016.01)
*G06N 3/084* (2023.01)
*G06T 7/00* (2017.01)
*G06V 10/80* (2022.01)
*G06V 20/52* (2022.01)

(52) U.S. Cl.
CPC ............ *G06V 10/809* (2022.01); *G06V 20/52* (2022.01); *A61B 5/06* (2013.01); *A61B 6/12* (2013.01); *A61B 8/0841* (2013.01); *A61B 8/463* (2013.01); *A61B 2034/2065* (2016.02); *G06T 2207/20084* (2013.01); *G06T 2207/30021* (2013.01)

(58) Field of Classification Search
CPC .... G06V 2201/031; G06T 2207/20084; G06T 2207/30021
See application file for complete search history.

(56) References Cited

U.S. PATENT DOCUMENTS

| | | | |
|---|---|---|---|
| 8,867,802 | B2 | 10/2014 | Criminisi et al. |
| 9,153,022 | B2 | 10/2015 | Finkelstein et al. |
| 9,256,962 | B2 | 2/2016 | Berry et al. |
| 9,384,413 | B2 | 7/2016 | John et al. |
| 2003/0133611 | A1 | 7/2003 | Deco et al. |
| 2003/0174881 | A1 | 9/2003 | Simard et al. |
| 2008/0101676 | A1* | 5/2008 | Zheng ................. G06T 7/12 382/131 |
| 2010/0010348 | A1 | 1/2010 | Halmann |
| 2011/0182493 | A1 | 7/2011 | Huber et al. |
| 2011/0188715 | A1 | 8/2011 | Shotton et al. |
| 2013/0336553 | A1 | 12/2013 | Buisseret et al. |
| 2014/0011173 | A1* | 1/2014 | Tepper ............. G09B 23/281 434/273 |
| 2014/0129200 | A1 | 5/2014 | Bronstein et al. |
| 2014/0314290 | A1 | 10/2014 | Dabbah et al. |
| 2015/0086091 | A1* | 3/2015 | Rezaee ............ G06F 18/2323 382/128 |
| 2015/0148657 | A1 | 5/2015 | Shashar et al. |
| 2015/0164605 | A1 | 6/2015 | Patwardhan et al. |
| 2015/0173701 | A1 | 6/2015 | Major et al. |
| 2015/0265251 | A1 | 9/2015 | Cho et al. |
| 2016/0012604 | A1 | 1/2016 | Firouzian et al. |
| 2016/0042510 | A1 | 2/2016 | Littel |
| 2016/0042511 | A1 | 2/2016 | Chukka et al. |
| 2016/0058422 | A1 | 3/2016 | Lee et al. |
| 2016/0092748 | A1 | 3/2016 | Koktava et al. |
| 2016/0106321 | A1 | 4/2016 | Sharma et al. |
| 2016/0125595 | A1 | 5/2016 | Silbert et al. |
| 2016/0174902 | A1 | 6/2016 | Georgescu et al. |
| 2016/0287214 | A1 | 10/2016 | Ralovich et al. |
| 2016/0317118 | A1 | 11/2016 | Parthasarathy et al. |
| 2016/0328643 | A1 | 11/2016 | Liu et al. |
| 2017/0163359 | A1* | 6/2017 | Fraiser ................. H04B 17/29 |
| 2019/0122073 | A1* | 4/2019 | Ozdemir ............... G06V 20/56 |
| 2019/0313986 | A1* | 10/2019 | Do ........................ A61B 6/12 |
| 2019/0384986 | A1* | 12/2019 | Chen .................... G06V 40/67 |
| 2021/0290317 | A1* | 9/2021 | Sen ...................... G06N 3/047 |
| 2021/0307841 | A1* | 10/2021 | Buch ..................... A61B 5/749 |

FOREIGN PATENT DOCUMENTS

| | | | |
|---|---|---|---|
| WO | WO 2013/179188 A1 | 12/2013 | |
| WO | WO-2014138652 A1 * | 9/2014 | ............ A61B 34/20 |
| WO | WO 2015/092582 A1 | 6/2015 | |
| WO | WO 2015/104607 A1 | 7/2015 | |
| WO | WO 2015/109254 A2 | 7/2015 | |
| WO | WO 2015/175806 A1 | 11/2015 | |
| WO | WO 2015/191414 A2 | 12/2015 | |
| WO | WO 2018/009405 * | 1/2018 | ............... G06K 9/32 |
| WO | WO-2018009405 A1 * | 1/2018 | ........... G06K 9/3233 |
| WO | WO 2018/101985 A1 * | 6/2018 | ............... G06T 7/73 |

OTHER PUBLICATIONS

Hadjerci et al., "On-line Learning Dynamic Models for Nerve Detection in Ultrasound Videos", 2016 IEEE International Conference on Image Processing, Sep. 25, 2016, pp. 131-135.

Hoey et al., "Semi-supervised learning of a POMDP model of Patient-Caregiver Interactions", IJCAI Workshop on Modeling Others from Observations, Jul. 30, 2005, 9 pages.

Hong et al., "Decoupled Deep Neural Network for Semi-supervised Semantic Segmentation", Advances in Neural Information Processing Systems 28, Dec. 7, 2015, pp. 1-9.

Reddy D. Manikanta, "On segmentation of Nerve Structures in Ultrasound Images", retrieved from the Internet: https://manikantareddyd.github.io/posts/2016/11/16/ultrasound-nerve-segmentations, Nov. 16, 2016, pp. 1-27.

International Search Report and Written Opinion for PCT/US2020/046432, dated Nov. 4, 2020, 13 pages.

* cited by examiner

SYSTEM AND METHOD FOR IDENTIFICATION, LABELING, AND TRACKING OF A MEDICAL INSTRUMENT

FIELD OF THE INVENTION

The present invention relates to object detection in the field of medical imaging, and more particularly, to a system and method for the detection, visualization, and tracking of one or more objects of interest (e.g., a medical instrument and optionally one or more anatomical objects) using machine learning, image processing and computer vision algorithms.

BACKGROUND

Detecting and segmentation of medical instruments and anatomical objects is an essential task in medical imaging that supports clinical imaging workflow from diagnosis, patient stratification, therapy planning, intervention, and/or follow-up. As such, it is important that the visualization and tracking of medical instruments and the visualization of anatomical objects and surrounding tissue occurs quickly, accurately, and robustly.

Various systems based on traditional approaches exist for addressing the problem of the detection and tracking of objects of interest (e.g., medical instruments, anatomical in medical images, such as computed tomography (CT), magnetic resonance (MR), ultrasound, and fluoroscopic images. However, anatomical object detection using such systems is not always robust, especially for some challenging detection problems in which the anatomical objects exhibit large variations in anatomy, shape, and/or appearance, as well as noise and artifacts in the medical images. For example, for certain nerve block procedures, it is often difficult for a physician to quickly and accurately locate a nerve bundle via an ultrasound imaging system. It is also extremely difficult for such systems to identify, much less track, a small medical instrument such as a needle or probe used to deliver nerve blocks or other therapy to a nerve block or other anatomical structure. As such, there is a need in the medical field for an imaging system that can visualize and track small medical instruments in real-time using existing imaging equipment and computing systems and that can also visualize one or more anatomical objects at the same time.

Accordingly, the present disclosure is directed to a system and method for the visualization and tracking of medical instruments and the visualization of anatomical objects using machine-learned models that can be implemented via existing imaging and/or computing systems and that can be machine agnostic.

SUMMARY OF THE INVENTION

Objects and advantages of the invention will be set forth in part in the following description, or may be obvious from the description, or may be learned through practice of the invention.

In one particular embodiment, a method for labeling a medical instrument in at least one image generated by an imaging system is provided. The method includes obtaining, by a computing system comprising one or more computing devices, patient imaging data including the least one image; inputting, by the computing system, the patient imaging data into a machine-learned medical instrument identification model; and receiving, by the computing system as an output of the machine-learned medical instrument identification model, a first label on the at least one image, wherein at least a portion of the medical instrument is labeled via the first label.

In another embodiment, the machine-learned medical instrument identification model can include one or more of a convolutional neural network and a recurrent neural network.

In still another embodiment, the first label can identify a tip of the medical instrument.

In yet another embodiment, the method can include inputting, by the computing system, the patient imaging data into a machine-learned anatomical object of interest identification model. Further, the machine-learned anatomical object of interest identification model can include one or more of a convolutional neural network and a recurrent neural network.

In addition, the method can also include receiving, by the computing system as an output of the machine-learned anatomical object of interest identification model, a second label on the at least one image, wherein at least a portion of the anatomical object of interest is labeled via the second label, wherein the first label and the second label are overlaid onto the at least one image in real-time. Further, the first label can be visually distinguishable from the second label.

In one more embodiment, the imaging system can include one or more of an ultrasound imaging system, a computer tomography scanner, and a magnetic resonance imaging scanner.

In an additional embodiment, the method can include displaying the labeled image to a user.

In one more embodiment, the computing system can be separate from the imaging system.

In yet another embodiment, the computing system can be a part of the imaging system.

In another particular embodiment, the present invention is directed to a computing system. The computing system includes a machine-learned medical instrument identification model trained to label at least a portion of a medical instrument based on patient imaging data containing at least one image; one or more processors; one or more non-transitory computer-readable media that store instructions that, when executed by the one or more processors, cause the one or more processors to perform operations, the operations comprising: obtaining the patient imaging data containing the at least one image; inputting the patient imaging data containing the at least one image into the machine-learned medical instrument identification model; and receiving, as an output of the machine-learned medical instrument identification model, a first label on the image, wherein at least a portion of the medical instrument is labeled via the first label; and a display configured to display the labeled image to a user.

In one embodiment, the machine-learned medical instrument identification model can include one or more of a convolutional neural network and a recurrent neural network.

In another embodiment, the first label can identify a tip of the medical instrument.

In still another embodiment, the computer system can further include a machine-learned anatomical object of interest identification model trained to label at least a portion of an anatomical object of interest based on the patient imaging data containing the at least one image. Further, the machine-learned anatomical object of interest identification model can include one or more of a convolutional neural network and a recurrent neural network.

In yet another embodiment, the operations can further include inputting the patient imaging data containing the at least one image into the machine-learned anatomical object of interest identification model; and receiving, as an output of the machine-learned anatomical object of interest identification model, a second label on the image, wherein at least a portion of the anatomical object of interest is labeled via the second label, wherein the first label and the second label are overlaid onto the at least one image in real-time. In addition, the first label can be visually distinguishable from the second label.

In one more embodiment, the computing system can be a part of an imaging system.

In an additional embodiment, the imaging system can include one or more of an ultrasound imaging system, a computer tomography scanner, and a magnetic resonance imaging scanner.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1A:
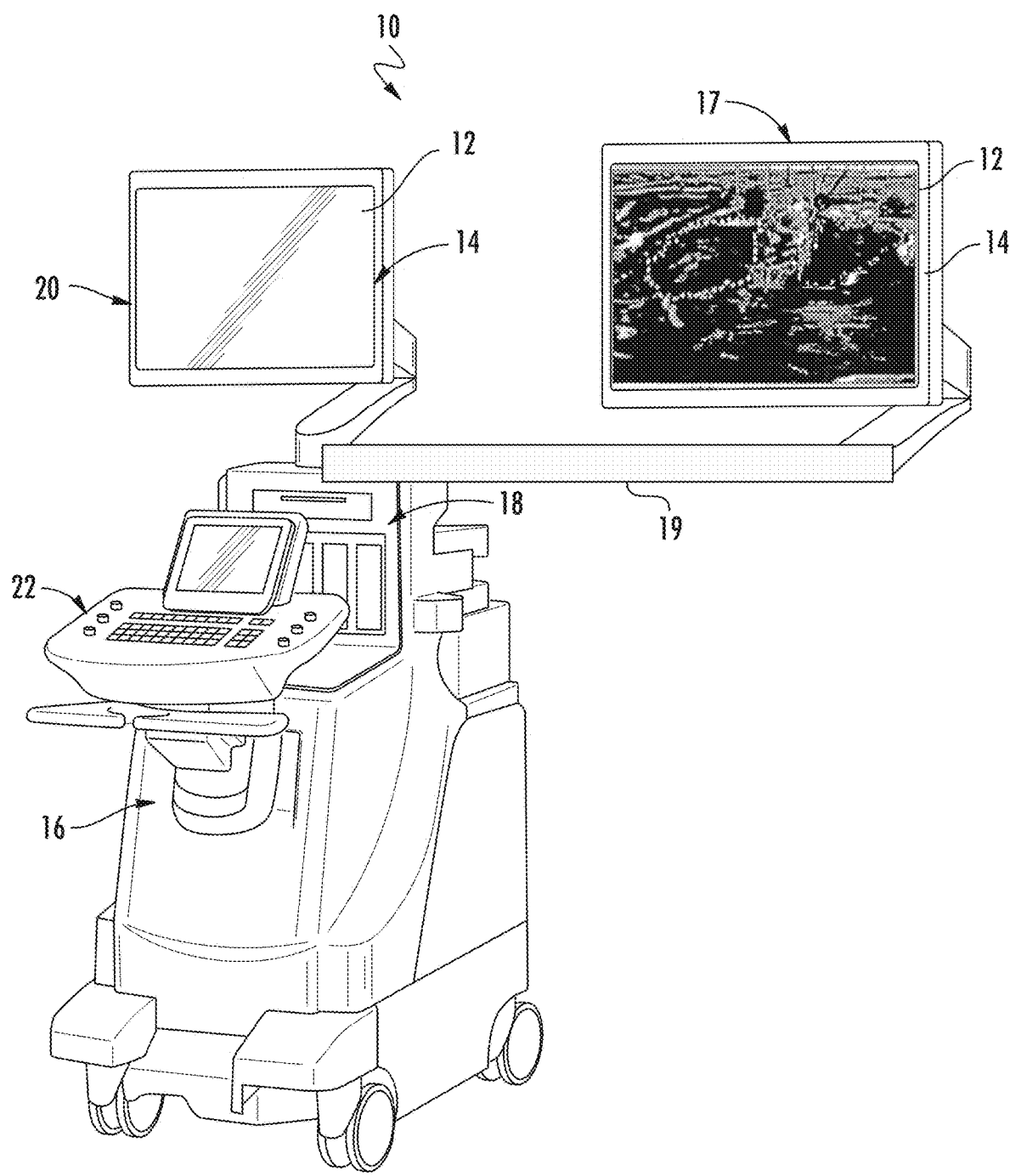
FIG. 1A illustrates a perspective view of one embodiment of an imaging system according to the present disclosure.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Figure 6:
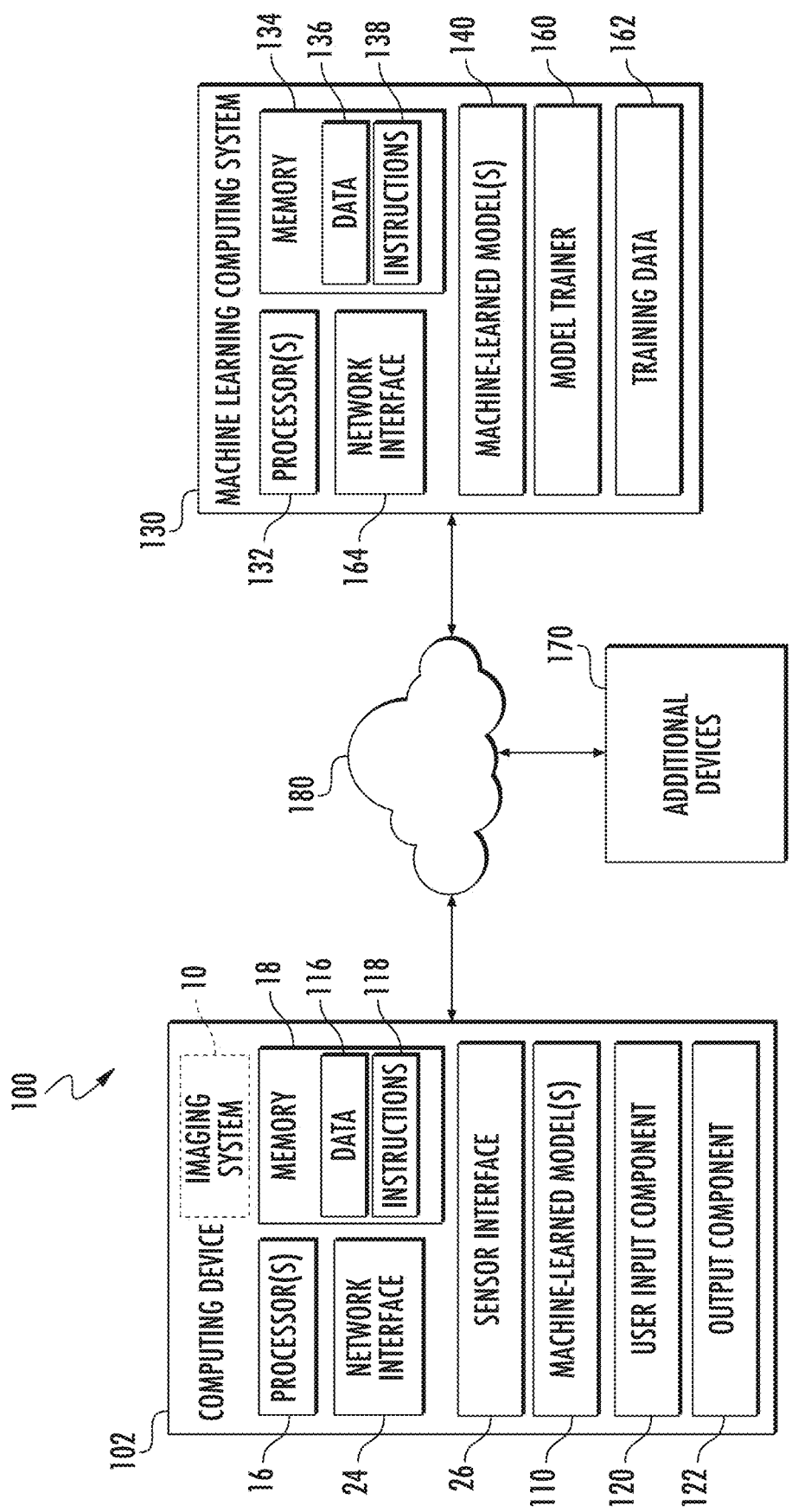
FIG. 6 illustrates an example computing system for machine-learning-based object identification according to one embodiment of the present disclosure, where the computing system of FIG. 6 may be an integral or separate component of the imaging system of FIGS. 1A and 1B.

Generally, the present disclosure is directed to a system and method for the automatic localization and tracking of one or more medical instruments (e.g., a needle, catheter, introducer, probe, etc.) and optionally the automatic localization of one or more anatomical objects in a scene of an image generated by an imaging system, such as an ultrasound imaging system. More specifically, referring now to the drawings, FIGS. 1A, 1B, and 2 illustrate exemplary embodiments of a standard imaging system 10 and a mobile device imaging system 11 configured to receive and organize a plurality of individual images 14 generated by the imaging system 10 or 11 in real-time in conjunction with a computing system 100 as shown in FIG. 6, where it is to be understood that the computing system 100 may be an integral component of the imaging system 10 or 11 or a separate component.

As used herein and as shown in FIG. 1A, the imaging system 10 may correspond to a standard ultrasound imaging system (as shown), a computer tomography (CT) scanner, a magnetic resonance imaging (MRI) scanner, or any other suitable imaging system that can benefit from the present technology. More specifically, as shown, the imaging system 10 can include a controller/processor 16 configured to receive and organize the plurality of individual images 14 generated by the imaging system 10. The controller/processor 16 generally includes one or more associated memory device(s) 18 configured to perform a variety of computer-implemented functions (e.g., performing the methods and the like and storing relevant data as disclosed herein), as well as a user display 20. For instance, the controller/processor 16 can be configured to detect, identify, and map or track one or more objects (e.g., medical instruments, anatomical features, etc.) in a plurality of scenes 12 contained within each image 14 generated by the imaging system 10 from a plurality of real-time two-dimensional ultrasound images 70 extruded from a video feed 60 (see FIGS. 7 and 8). In addition, the imaging system 10 can include a user interface 22, such as a computer and/or keyboard, configured to assist a user in generating and/or manipulating the plurality of scenes 12 contained within each individual image 14. Further, the imaging system 10 can also include an additional display 17 that can depict annotated or labeled objects of interest (e.g., a medical instrument 145 or an anatomical object of interest) to localize and/or track such objects, although it is to be understood that in some embodiments, the user display 20 can be used to depict the annotated or labeled objects of interest. If an additional display 17 is utilized, the additional display 17 can be coupled to the rest of the imaging system via a mechanical arm 19 so that a user (e.g., healthcare provider) can position the additional display 17 in a desired location for ease of viewing the annotated image 14.

Figure 1B:
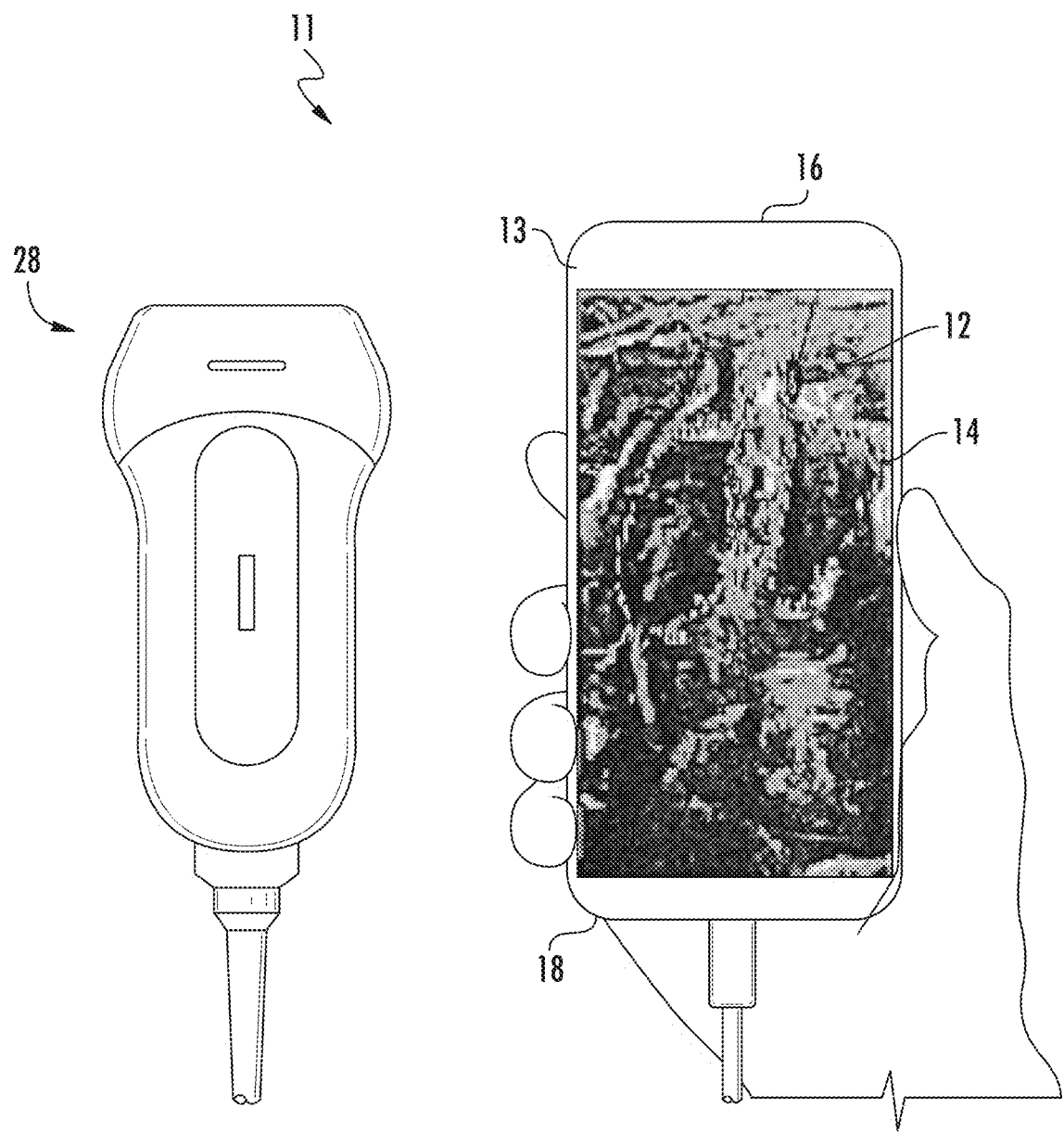
FIG. 1B illustrates a perspective view of another embodiment of an imaging system according to the present disclosure.

Meanwhile, as shown in FIG. 1B, the imaging system 11 may correspond to a mobile imaging system, such as an ultrasound imaging system that can be in the form of a cellular device or tablet that is portable. Like the standard imaging system 10, the mobile imaging system 11 may correspond to an ultrasound imaging system (as shown), a computer tomography (CT) scanner, a magnetic resonance imaging (MRI) scanner, or any other suitable imaging system that can benefit from the present technology. More specifically, as shown, the imaging system 11 can include a controller/processor 16 configured to receive and organize the plurality of individual images 14 generated by the imaging system 11. The controller/processor 16 generally includes one or more associated memory device(s) 18 configured to perform a variety of computer-implemented functions (e.g., performing the methods and the like and storing relevant data as disclosed herein), as well as a user display 13. For instance, the controller/processor 16 can be configured to detect, identify, and map or track one or more objects (e.g., medical instruments, anatomical features, etc.) in a plurality of scenes 12 contained within each image 14 generated by the imaging system 11 from a plurality of real-time two-dimensional ultrasound images 70 extruded from a video feed 60 (see FIGS. 7 and 8). In addition, the imaging system 11 can include a touch screen user interface (not shown) configured to assist a user in generating and/or manipulating the plurality of scenes 12 contained within each individual image 14.

Figure 2:
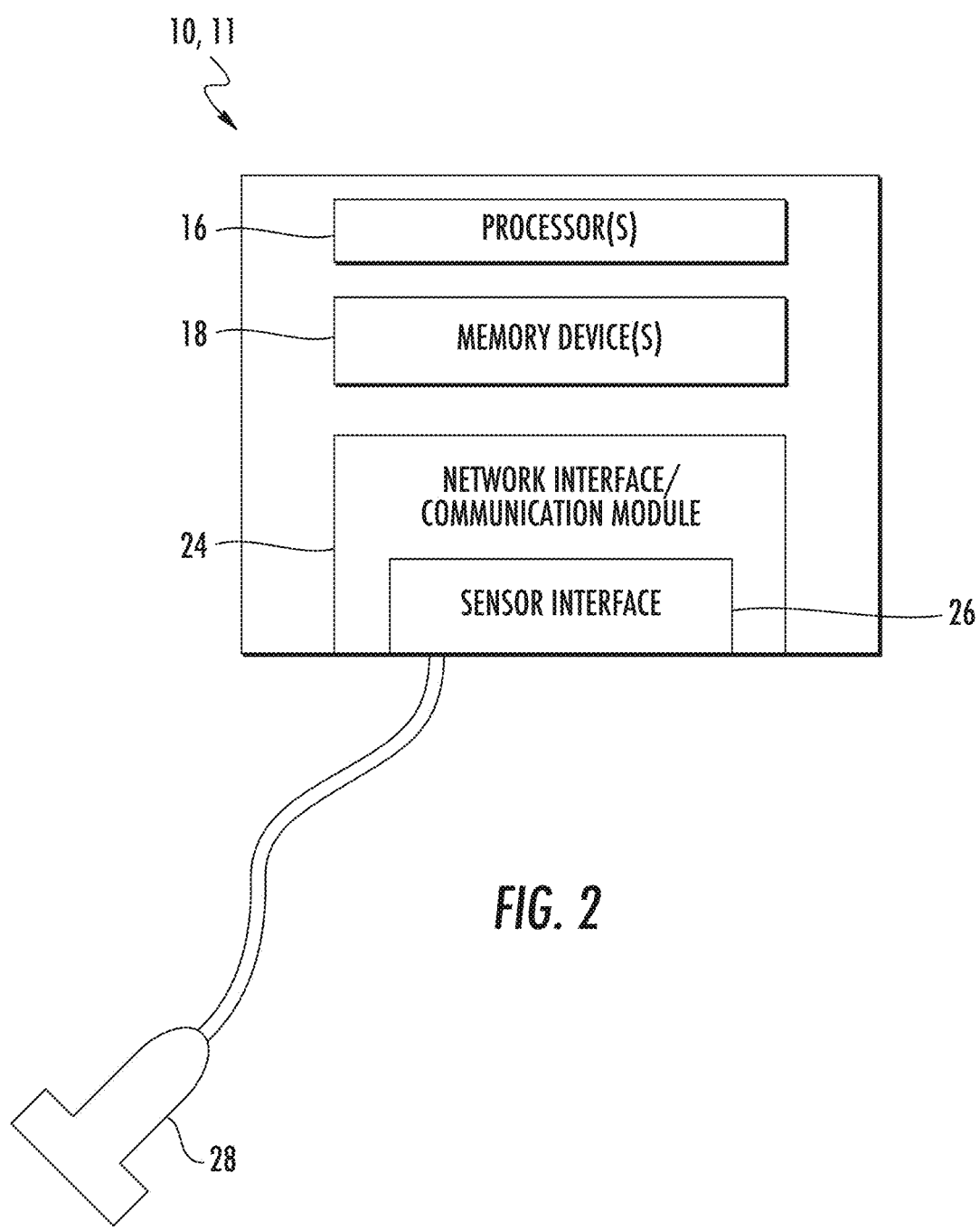
FIG. 2 illustrates a block diagram of one embodiment of a processor and probe of an imaging system according to the present disclosure.

Additionally, as shown in FIG. 2, the controller/processor 16 may also include a communications module or network interface 24 to facilitate communications between the controller/processor 16 and the various components of the computing system 100 and/or imaging system 10 or 11, e.g. any of the components of FIGS. 1A-3 and 6-8. Further, the communications module or network interface 24 may include a sensor interface 26 (e.g., one or more analog-to-digital converters) to permit signals transmitted from one or more imaging system probes 28 (e.g., the ultrasound probe) to be converted into signals that can be understood and processed by the controller/processor(s) 16. It should be appreciated that the probe 28 may be communicatively coupled to the communications module or network interface/communications module 24 using any suitable means. For example, as shown in FIG. 2, the probe 28 may be coupled to the sensor interface 26 via a wired connection. However, in other embodiments, the probe 28 may be coupled to the sensor interface 26 via a wireless connection, such as by using any suitable wireless communications protocol known in the art. As such, the controller/processor 16 may be configured to receive one or more signals from the probe 28.

As used herein, the term "controller" refers not only to integrated circuits referred to in the art as being included in a computer, but also refers to a microcontroller, a microcomputer, a programmable logic controller (PLC), an application specific integrated circuit, a field-programmable gate array (FPGA), and other programmable circuits. In other words, the controller/processor 16 can be any suitable processing device (e.g., a processor core, a microprocessor, an ASIC, a FPGA, a controller, a microcontroller, etc.) and can be one processor or a plurality of processors that are operatively connected. The controller/processor 16 may also configured to compute advanced control algorithms and communicate to a variety of Ethernet or serial-based protocols (Modbus, OPC, CAN, etc.). Furthermore, in certain embodiments, the controller/processor 16 may communicate with a server through the Internet for cloud computing in order to reduce the computation time and burden on the local device. Additionally, the memory device(s) 18 may generally comprise memory element(s) including, but not limited to, one or more non-transitory computer-readable storage media, such as RAM, ROM, EEPROM, EPROM, one or more memory devices, flash memory devices, etc., and combinations thereof. Such memory device(s) 18 may generally be configured to store suitable computer-readable instructions that, when implemented by the controller/processor(s) 16, configure the controller/processor(s) 16 to perform the various functions as described herein.

Figure 3:
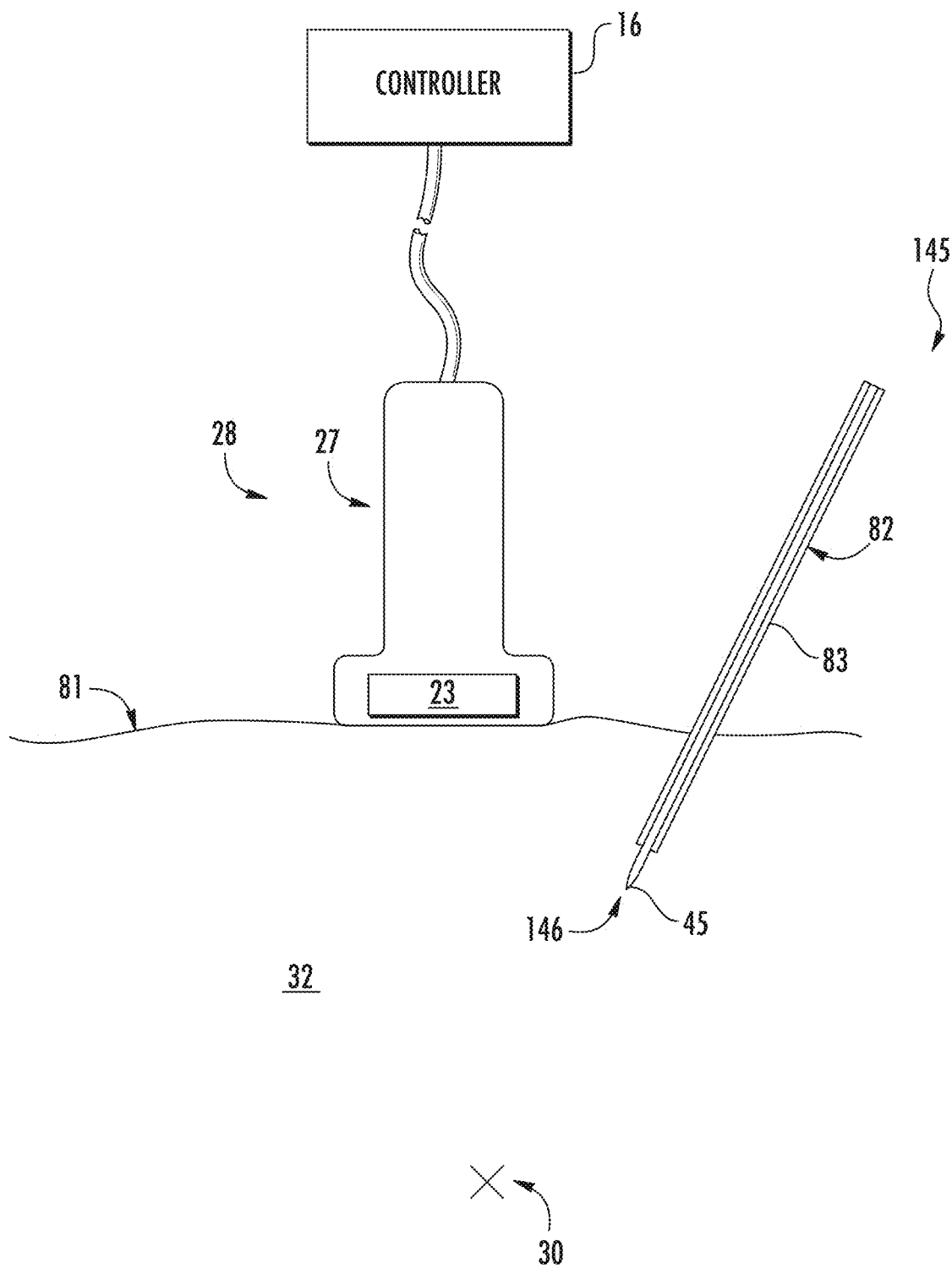
FIG. 3 illustrates a schematic diagram of one embodiment of an ultrasound imaging system according to the present disclosure, particularly illustrating an ultrasound probe used in conjunction with a needle guide to facilitate navigation of a needle towards a target nerve of a patient.

Turning now to FIG. 3, when the imaging system 10 or 11 is an ultrasound imaging system, the probe 28 (e.g., ultrasound probe) of the imaging system 10 or 11 can include a transducer housing 27 and a transducer transmitter 23 mounted therein. As is generally understood, the transducer transmitter 23 is configured to emit and/or receive ultrasound beams. As such, the transducer transmitter 23 may be configured within the internal cavity (not numbered) such that the transducer transmitter 23 is configured to scan an anatomical region surrounding a target anatomical object 30 (e.g., target nerve) of a patient. The imaging system 10 or 11 is used in conjunction with any medical instrument 145 that may be used during a medical procedure, where the instrument 145 can be located and easily tracked with visual cues (e.g., labels, outlines, etc.) via the methods described herein. When the medical procedure is a nerve block procedure, the instrument 145 can be a needle guide assembly 82, and the controller/processor 16 can be configured to locate, identify, label, and track the needle guide assembly 82 as it is being moved towards a target anatomical object 30 (e.g., the target nerve) that may also be located, identified, and labeled to deliver, for instance, an anesthetic via a needle 45. It is to be understood, however, that any instrument such as a scalpel, knife, laparoscopic or arthroscopic probe, etc. can be used instead of the needle guide assembly 82 depending on the procedure being performed by the medical professional.

More specifically, as shown, the needle guide assembly 82 may include, at least, a needle 45 and a catheter 83. As such, it should be understood that the needle 45 as well as the catheter 83 of the needle guide assembly 82 can be inserted through a patient's skin surface 81 in any particular order or simultaneously. For example, in one embodiment, the ultrasound imaging system 10 or 11 may be used in conjunction with an over-the-needle (OTN) catheter assembly in which the catheter 83 is coaxially mounted over the needle 45. Alternatively, the needle 45 may be mounted over the catheter 83. In such embodiments, the needle 45 may act as an introducer such that it places the catheter 83 at the target nerve 49 and is later removed.

Figure 4:
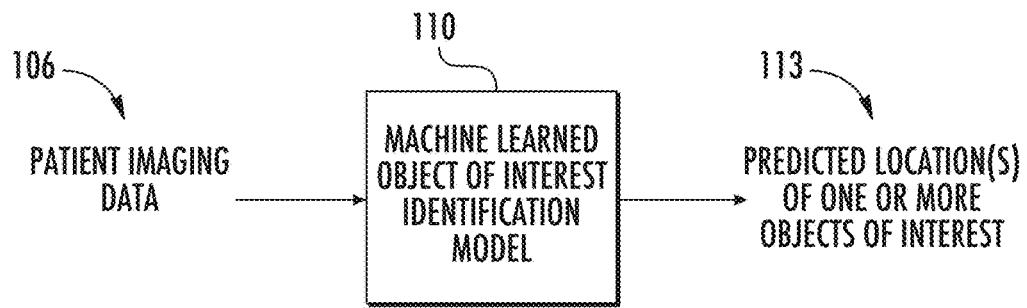
FIG. 4 illustrates an example processing workflow for identification of one or more objects of interest (e.g., a medical instrument, anatomical object, etc.) according to one embodiment of the present disclosure.

Turning now to FIG. 4, a process flow diagram exemplifying how the computing system 100, that can include the imaging system 10 or 11 described above, can be utilized to identify, visualize/label, and track a medical instrument and optionally identify and visualize/label one or more anatomical objects is described in detail. Specifically, FIG. 4 depicts an example processing workflow for identification of an object or objects of interest (e.g., a medical instrument and one or more anatomical objects) according to one embodiment of the present disclosure. In particular, the processing workflow includes or otherwise utilizes a machine-learned object of interest identification model 110.

A health care provider or other individual can use the imaging system 10 or 11 described above to acquire one or more ultrasounds images, which can be in the form of a video feed 60 that is then segmented into a plurality of two-dimensional initial images 70 (see FIGS. 7 and 8) from the patient to generate the patient imaging data 106 associated with the patient. The health care provider can then input the imaging data 106 from the imaging system 10 or 11 into the computing system 100 or the imaging data 106 can be collected by the computing system 100 automatically (e.g., through the imaging system software and hardware associated with the computing system 100).

As one example, the one or more images can include one or more ultrasound, CT, MRI, or fluoroscopic images that can be grouped as the patient imaging data 106. The patient imaging data 106 can include images of a medical instrument and/or anatomical objects of interest that the health care provider would ultimately like to accurately identify/visualize and track.

The computing system 100 can then input the patient imaging data 106 for any of a number of patients into the machine-learned object identification model 110. As examples, the machine-learned object identification model 110 can include a deep artificial neural network, a support vector machine, a decision tree, and/or a linear model.

The machine-learned object identification model 110 can then output one or more predicted locations of one or more objects of interest 113 when a new image or series of images from an individual (e.g., initial images 70 in FIG. 8) are acquired utilizing the patient imaging data 106 that has been input into the machine-learned object identification model 110. The output can be in the form of one or more labeled or annotated images 80 that include a label around the object of interest, shading of the one or more objects of interest, or any other visual cue that alerts a health care provider of the location of the one or more objects of interest. Further, when two or more objects of interest are labeled, the labels can be visually distinguishable from each other (e.g., dashed outlining versus solid outlining, shading versus outlining, different colors, etc.)

Referring still to FIG. 4, in some embodiments, the output of the machine-learned model 110 (e.g., identification of the predicted location of one or more objects of interest) can further include or depict probability information that describes, for each predicted location of the object of interest 113 on a newly acquired image, a probability that the object of interest has been correctly identified and/or located in the scene of an acquired image. Thus, the machine-learned model 110 can identify the various locations of one or more objects of interest that a health care provider can use during a medical procedure to ensure accurate placement of a medical instrument near a specific tissue, muscle, nerve, bone, etc. while avoiding other anatomical regions.

Figure 5:
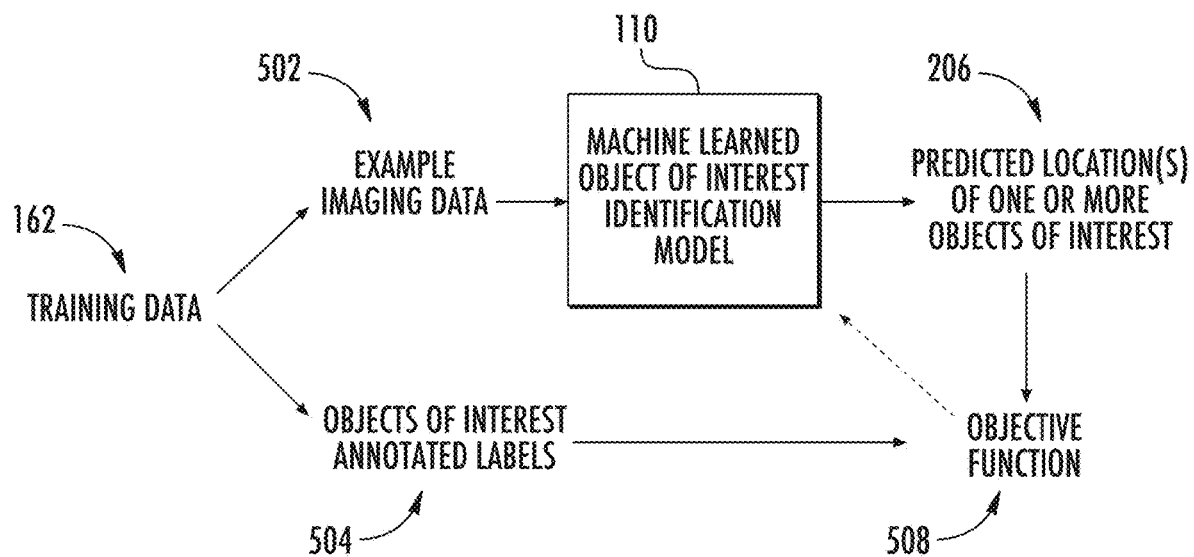
FIG. 5 illustrates an example processing workflow for training an object of interest identification model according to one embodiment of the present disclosure.

FIG. 5 depicts an example workflow for training a machine-learned object identification model 110 according to one embodiment of the present disclosure. For example, the workflow can be performed by a machine learning computing system 100 (e.g., the model trainer 160 of machine learning computing system 140, as described below with reference to FIG. 6). In some embodiments, the machine-learned object of interest identification model 110 can be trained on training data 162. The training data 162 can includes sets of example imaging data 502 that are annotated with labels 504 to identify one or more objects of interest. That is, each set of example imaging data 502 can have an associated label or labels 504 that describe the location of one or more objects of interest associated with a patient that generated the corresponding example imaging data 502.

The example imaging data 502 can include any of the types of imaging data described with reference to FIG. 4. The object of interest labels 504 can describe the location of the one or more objects of interest in any of the forms described with reference to FIG. 4. For example, the object of interest labels 504 can mirror the format for which the objects of interest in the patient imaging data of FIG. 4 are desired to be represented. As one example, if it is desired for the model 110 to identify an object of interest in the form of an outline or shading, then the object of interest labels 504 can be or include ground truth outlines or shading associated with the example imaging data 502.

In one embodiment, the training data 162 can be obtained from a database where health care providers upload images and then manually annotate those images to identify known objects of interest (e.g., specific anatomical parts, medical instruments, etc.) Each set of example imaging data 502 can be input into the object identification model 110. In response, the model 110 can output one or more predicted locations of one or more objects of interest 506 for each set of example imaging data 502. An objective function 508 can evaluate a difference between the identified predicted location(s) of one or more objects of interest 506 for each set of example imaging data 502 and the object of interest label(s) 504 associated with such set of imaging data 502. For example, the identified objects of interest labels 504 can be compared to the ground truth labels. As one example, the objective function 508 can determine, for each pixel or voxel of a rendering of the surrounding tissue in an image, whether the identification of the object of interest matches the label for such pixel or voxel, where non-matching pixels/voxels increase a loss value. The objective function 508 can be backpropagated through the object identification model 110 to train the model 110. It should be understood that FIG. 5 illustrates one example supervised learning workflow. Other training techniques can be used in addition or alternatively to the example workflow shown in FIG. 5.

FIG. 6 depicts an example computing system 100 for machine-learning-based identification of brain injury locations according to example embodiments of the present disclosure. The example system 100 includes a computing device 102 and a machine learning computing system 130 that may communicatively coupled over a network 180 or that can be integrated into a single system 100 that may also include the image system 10.

The computing device 102 includes one or more controllers/processors 16 and a memory 18. The one or more processors 16 can be any suitable processing device (e.g., a processor core, a microprocessor, an ASIC, a FPGA, a controller, a microcontroller, etc.) and can be one processor or a plurality of processors that are operatively connected. The memory 18 can include one or more non-transitory computer-readable storage media, such as RAM, ROM, EEPROM, EPROM, one or more memory devices, flash memory devices, etc., and combinations thereof.

The memory 18 can store information that can be accessed by the one or more controllers/processors 16. For instance, the memory 18 (e.g., one or more non-transitory computer-readable storage mediums, memory devices) can store data 116 that can be obtained, received, accessed, written, manipulated, created, and/or stored. In some implementations, the computing device 102 can obtain data from one or more memory device(s) that are remote from the device 102.

The memory 18 can also store computer-readable instructions 118 that can be executed by the one or more controllers/processors 16. The instructions 118 can be software written in any suitable programming language or can be implemented in hardware. Additionally, or alternatively, the instructions 118 can be executed in logically and/or virtually separate threads on processor(s) 16. For example, the memory 18 can store instructions 118 that when executed by the one or more processors 16 cause the one or more processors 16 to perform any of the operations and/or functions described herein.

According to an aspect of the present disclosure, the computing device 102 can store or include one or more machine-learned models 110. For example, the models 110 can be or can otherwise include various machine-learned models such as a random forest classifier; a logistic regression classifier; a support vector machine; one or more decision trees; a neural network; and/or other types of models including both linear models and non-linear models. Example neural networks include feed-forward neural networks, recurrent neural networks (e.g., long short-term memory recurrent neural networks), convolutional neural networks, or other forms of neural networks.

In some implementations, the computing device 102 can receive the one or more machine-learned models 110 from the machine learning computing system 130 over network 180 and can store the one or more machine-learned models 110 in the memory 18. The computing device 102 can then use or otherwise run the one or more machine-learned models 110 (e.g., by processor(s) 16).

The machine learning computing system 130 can include one or more processors 132 and a memory 134. The one or more processors 132 can be any suitable processing device (e.g., a processor core, a microprocessor, an ASIC, a FPGA, a controller, a microcontroller, etc.) and can be one processor or a plurality of processors that are operatively connected. The memory 134 can include one or more non-transitory computer-readable storage media, such as RAM, ROM, EEPROM, EPROM, one or more memory devices, flash memory devices, etc., and combinations thereof.

The memory 134 can store information that can be accessed by the one or more processors 132. For instance, the memory 134 (e.g., one or more non-transitory computer-readable storage mediums, memory devices) can store data 136 that can be obtained, received, accessed, written, manipulated, created, and/or stored. In some implementations, the machine learning computing system 130 can obtain data from one or more memory device(s) that are remote from the system 130. The memory 134 can also store computer-readable instructions 138 that can be executed by the one or more processors 132. The instructions 138 can be software written in any suitable programming language or can be implemented in hardware. Additionally, or alternatively, the instructions 138 can be executed in logically and/or virtually separate threads on processor(s) 132. For example, the memory 134 can store instructions 138 that when executed by the one or more processors 132 cause the one or more processors 132 to perform any of the operations and/or functions described herein.

In some implementations, the machine learning computing system 130 includes one or more server computing devices. If the machine learning computing system 130 includes multiple server computing devices, such server computing devices can operate according to various computing architectures, including, for example, sequential computing architectures, parallel computing architectures, or some combination thereof.

In addition or alternatively to the model(s) 110 at the computing device 102, the machine learning computing system 130 can include one or more machine-learned models 140. For example, the models 140 can be or can otherwise include various machine-learned models such as a random forest classifier; a logistic regression classifier; a support vector machine; one or more decision trees; a neural network; and/or other types of models including both linear models and non-linear models. Example neural networks include feed-forward neural networks, recurrent neural networks (e.g., long short-term memory recurrent neural networks), convolutional neural networks, or other forms of neural networks.

As an example, the machine learning computing system 130 can communicate with the computing device 102 according to a client-server relationship. For example, the machine learning computing system 130 can implement the machine-learned models 140 to provide a web service to the computing device 102. For example, the web service can provide identification of brain injury locations as a service. Thus, machine-learned models 110 can be located and used at the computing device 102 and/or machine-learned models 140 can be located and used at the machine learning computing system 130.

In some implementations, the machine learning computing system 130 and/or the computing device 102 can train the machine-learned models 110 and/or 140 through use of a model trainer 160. The model trainer 160 can train the machine-learned models 110 and/or 140 using one or more training or learning algorithms. One example training technique is backwards propagation of errors ("backpropagation").

In some implementations, the model trainer 160 can perform supervised training techniques using a set of labeled training data 162, for example as described with reference to FIG. 5. In other implementations, the model trainer 160 can perform unsupervised training techniques using a set of unlabeled training data. The model trainer 160 can perform a number of generalization techniques to improve the generalization capability of the models being trained. Generalization techniques include weight decays, dropouts, or other techniques. The model trainer 160 can be implemented in hardware, software, firmware, or combinations thereof.

As described above with respect to FIG. 6, the computing device 102 can also include a communication module or network interface 24 used to communicate with one or more systems or devices, including systems or devices that are remotely located from the computing device 102. The communications module or network interface 24 can include any circuits, components, software, etc. for communicating with one or more networks (e.g., 180). In some implementations, the network interface 24 can include, for example, one or more of a communications controller, receiver, transceiver, transmitter, port, conductors, software and/or hardware for communicating data. Similarly, the machine learning computing system 130 can include a communications module or network interface 164.

The computing device 102 can also include a sensor interface 26 as described above to permit signals transmitted from one or more imaging system probes 28 (e.g., the ultrasound probe) to be converted into signals that can be understood and processed by the controller and/or processor(s) 16, such as when the imaging system 10 or 11 and the computing system 100 and/or computing device 102 are integrated.

The computing device 102 can also include a user input component 120 similar to or including the user interface 22 of the imaging system 10 or 11. For example, the user input component 120 can include a microphone, a keypad, a keyboard, a click-wheel, buttons, and/or a touch-sensitive screen. The computing device 102 can also include an output component 122. For example, the output component 122 can include a speaker, a haptic output component, and/or a display (e.g., a touch-sensitive display).

As another example, the computing device 102 can transmit information to one or more additional devices 170 (e.g., a RF ablation system, databases, etc.). The computing device 102 can communicate with the additional computing device(s) 170 over the network 180 and/or via a local, short-range wireless communication protocol (e.g., Bluetooth). The network(s) 180 can be any type of network or combination of networks that allows for communication between devices. In some embodiments, the network(s) can include one or more of a local area network, wide area network, the Internet, secure network, cellular network, mesh network, peer-to-peer communication link and/or some combination thereof and can include any number of wired or wireless links. Communication over the network(s) 180 can be accomplished, for instance, via a network interface using any type of protocol, protection scheme, encoding, format, packaging, etc.

FIG. 6 illustrates one example computing system 100 that can be used to implement the present disclosure. Other computing systems can be used as well. For example, in some implementations, the computing device 102 can include the model trainer 160 and the training dataset 162 in addition to the imaging system 10 or 11, although it is to be understood that the imaging system 10 or 11 can be separate from the computing device 102. In such embodiments, the machine-learned models 110 can be both trained and used locally at the computing device 102. As another example, in some implementations, the computing device 102 is not connected to other computing systems.

Figure 7:
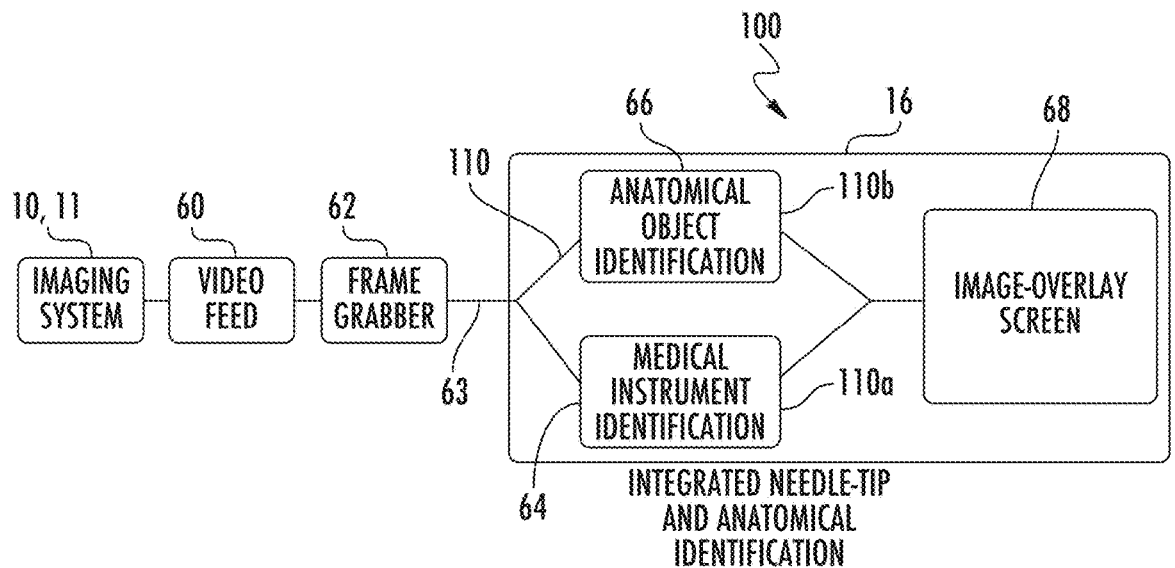
FIG. 7 illustrates a schematic diagram of a portion of the computing system of FIG. 6 for the identification of a medical instrument and an anatomical object according to one embodiment of the present disclosure.

FIG. 7 illustrates the relationship between the imaging system 10 or 11 of FIGS. 1A-3 and the computing system 100 of FIG. 6 in more detail, where it is to be understood that the imaging system 10 or 11 and the computing system 100 can be a part of an integral system or can be separate systems that are communicatively coupled. As shown in FIG. 7, the computing system 100 can receive a video feed 60 from the imaging system 10 or 11 in real-time via a cable 63, such as an HDMI, VGI, or DVI cable, and a frame grabber 62. Further, the frame grabber 62 can divide or segment the video feed 60 from the imaging system 10 or 11 into a plurality of individual two-dimensional images 70 (see FIG. 8) for processing by the processor 16 of the computing system 100. Then, the images 70 can be sent to a medical instrument identification processing block 64, an anatomical object identification processing block 64. Within the medical instrument identification processing block 64, the images 70 can be processed through a machine-learned medical instrument identification model 110a, and within the anatomical object identification block 64, the images 70 can be processed through a machine-learned anatomical object of interest identification model 110b that have been trained as described above with respect to FIGS. 5 and 6. Then, after the images 70 are processed via the machine-learned medical instrument identification model 110a and the machine-learned anatomical object of interest identification model 110b, the images 70 processed via the machine-learned medical instrument identification model 110a can be annotated or labeled to identify a medical instrument 145, and the images 70 processed via the machine-learned anatomical object identification model 110b can be annotated or labeled to identify one or more anatomical objects of interest 30, as well as other anatomical objects such as surrounding tissue 32. Further, the annotation or labeling is completed in real-time via the computing system 100 as a result of the processing of the images 70 through the machine-learned models 110 (e.g., models 110a and 110b, and any other models, such as a machine-learned surrounding tissue identification model (not shown)).

Once the images 70 are labeled to identify a medical instrument 145, an anatomical object of interest 30, and any other desired anatomical objects (e.g., surrounding tissue 32), the set of images 70 that have been labeled to identify a medical instrument 145 and the set of images 70 that have been labeled to identify an anatomical object of interest 30 and any other desired anatomical objects such as surrounding tissue 32 can be passed to an image overlay-screen 68 which combines the sets of images 70 to produce one or more label images 80 that include both the labels to identify the medical instrument 145 and the labels to identify the anatomical object of interest 30 and any other anatomical objects that are desired to be labeled. Further, at this point, a user can have the option to see a labeled image 80 of an individual overlay (e.g., to view only the medical instrument label 90 or only the anatomical object label 91) or to view both overlays (e.g., to view both the medical instrument label 90 and the anatomical object label 91), where if both overlays are included, the labels 90 and 91 are visually distinguishable.

Figure 8:
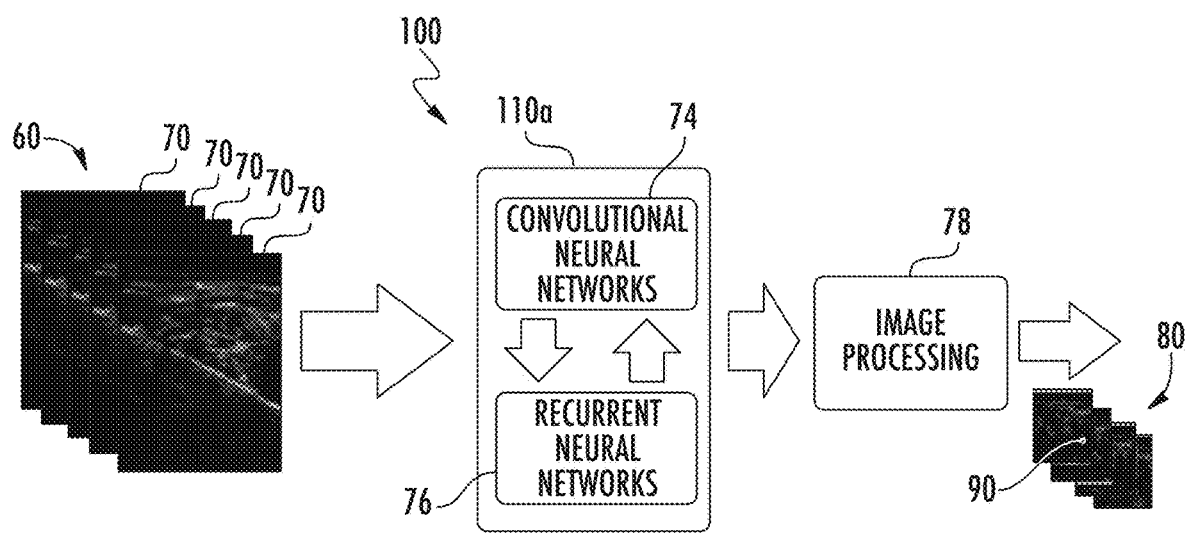
FIG. 8 illustrates a schematic diagram of a process for identification of an object of interest (e.g., a medical instrument or an anatomical object) using the computing system of FIG. 7 according to one embodiment of the present disclosure.
Figure 9:
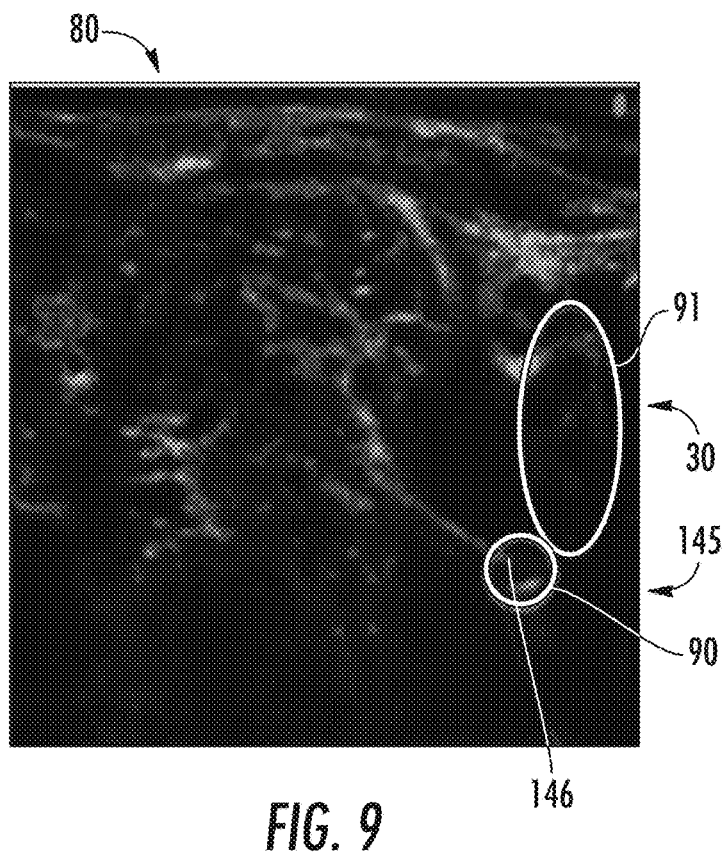
FIG. 9 illustrates an image generated by an imaging system according to the present disclosure, particularly illustrating both medical instrument and anatomical object localization of a patient with the tissue and tip of the medical instrument labeled or circled for ease of identification.
Figure 10:
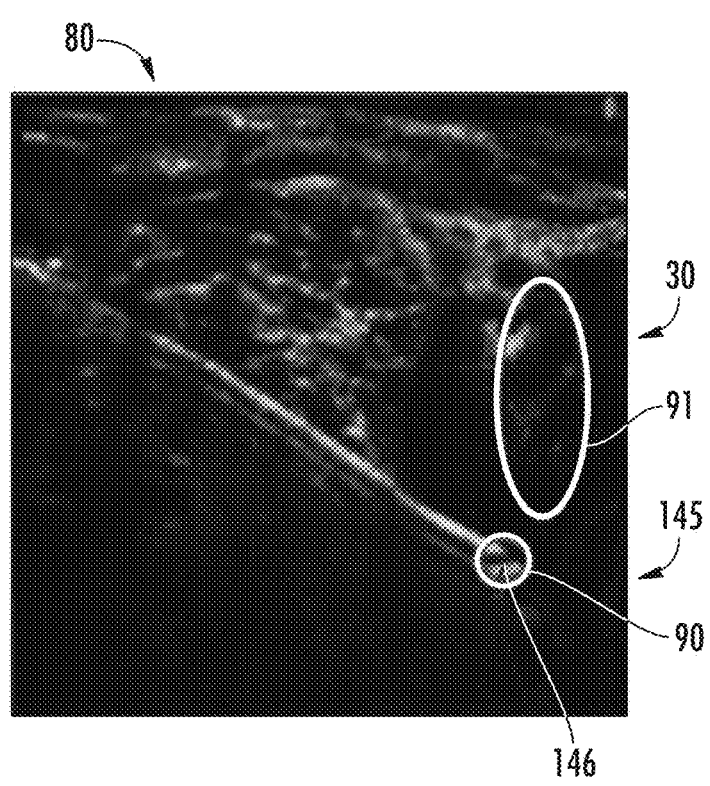
FIG. 10 illustrates another image generated by an imaging system according to the present disclosure, particularly illustrating both medical instrument and anatomical object localization of a patient with the tissue and tip of the medical instrument labeled or circled for ease of identification.
Figure 11:
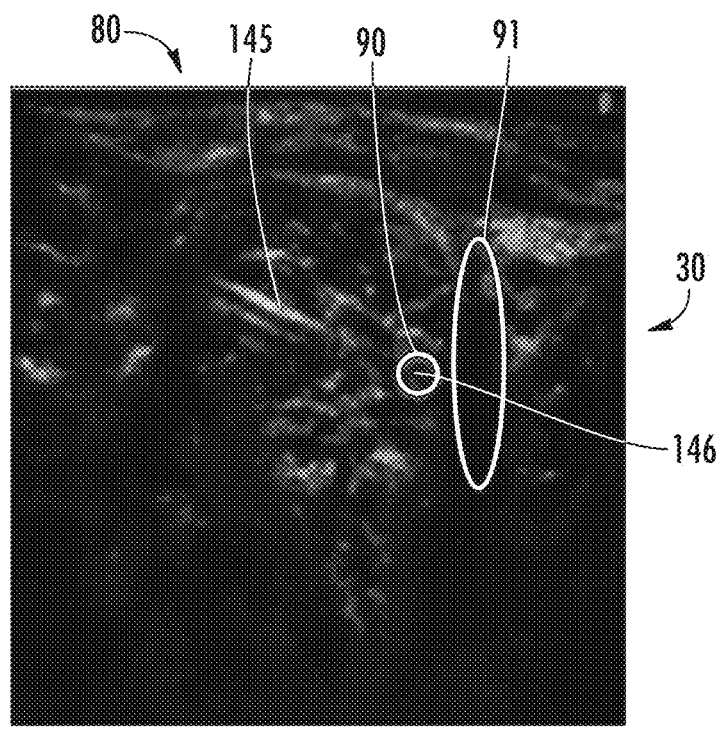
FIG. 11 illustrates yet another image generated by an imaging system according to the present disclosure, particularly illustrating both medical instrument and anatomical object localization of a patient with the tissue and tip of the medical instrument labeled or circled for ease of identification.
Figure 12:
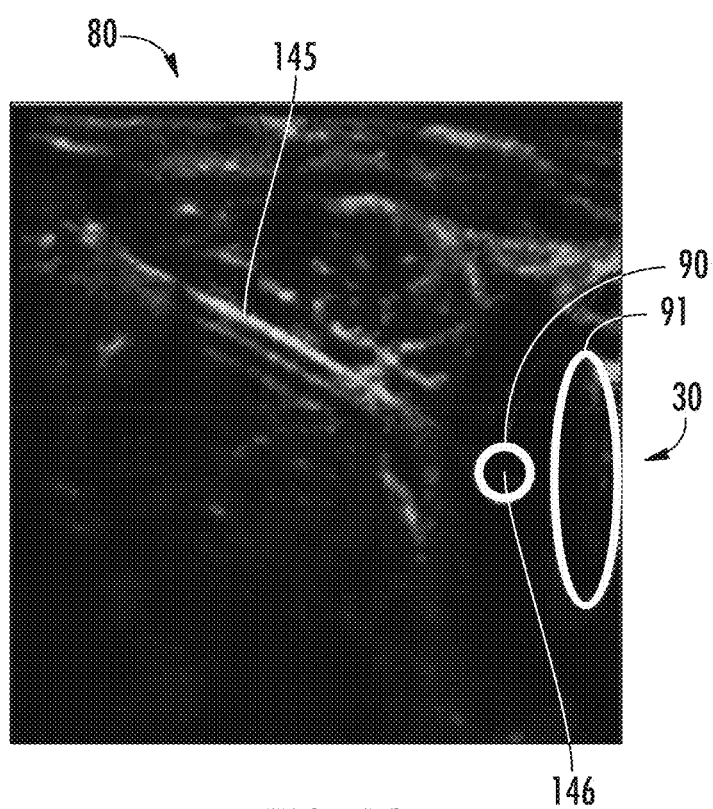
FIG. 12 illustrates still another image generated by an imaging system according to the present disclosure, particularly illustrating both medical instrument and anatomical object localization of a patient with the tissue and tip of the medical instrument labeled or circled for ease of identification.

FIG. 8 illustrates, for example, a block diagram for the real-time identification of a tip of medical instrument 145 via the methods contemplated by the present disclosure. For instance, the machine-learned medical instrument identification model 110a of the computing system 100 can process the video feed 60 containing initial images 70 from the imaging system 10 or 11 (see FIG. 7) in real-time to identify a tip of the medical instrument 145 and overlay a label 90 on one or more labeled images 80. After the machine-learned medical instrument identification model 110a identifies the tip 146 of the medical instrument 145, such as via one or more neural networks, such as convolutional neural networks 74 and recurrent neural networks 76, the images can be processed to overlay a label 90 of the identified instrument tip 146 onto the image 80. Further, it should be understood that the same method can be repeated for identification of one or more anatomical objects of interest 30 or any other anatomical objects such as surrounding tissue 32 via the machine-learned object of interest identification model 110b or any other machine-learned identification models, and it should also be understood that the processing of the images can be repeated to overlay more than one label on an individual image. For instance, both a label 90 of the identified instrument tip 146 and a label 91 of an anatomical object of interest 30 can be overlaid onto the same image 80.

FIGS. 9-12 show various labeled images 80 where a tip 146 of a medical instrument 145 is annotated with a label 90 and where an anatomical object of interest 30 is annotated with a label 91. Although not necessarily required, in some embodiments, the labels 90 and 91 can be different shades, colors, thicknesses, or line type to visually distinguish the instrument tip 146 from the anatomical object of interest 30. For instance, label 90 is a different shading and thickness compared to the label 91 in FIGS. 9-12. The labels 90 and 91 can be used to assist a health care provider to navigate the tip 146 of the instrument 145 to the anatomical object of interest 30 to, for instance, deliver medication or a nerve block from the tip 146 of the instrument 145 to the anatomical object of interest 30 (e.g., a nerve, muscle, other tissue, etc.) As shown, the shape of the medical instrument alone as generated by the ultrasound machine is somewhat blurry and grainy, and the label 90 overlaid onto the ultrasound image 80 by the systems and methods of the present disclosure allows the tip 146 of the instrument 145 to be easily identified. Thus, the health care provider can have greater assurance that any medication or nerve block delivered from the tip 146 is delivered directly to the anatomical object 30 of interest, as the systems and methods of the present disclosure allow for precise identification and visualization of the medical instrument 145 as it is being moved towards the anatomical object of interest 30.

Referring now to FIGS. 13-17, a flow diagram (FIG. 13) of one embodiment of a method 200 for identifying an object of interest (e.g., a medical instrument 145 and optionally at least one anatomical object 30) in a scene 12 of an ultrasound image 14 generated by an imaging system 10 or 11 is illustrated, as well as various embodiments of screen shots (FIGS. 14-17) from the user display 20, the add-on display 17, or the mobile display 13 depending on the particular imaging system utilized illustrating the scene 12 of the image 14. In certain embodiments, the anatomical object(s) 30 and the surrounding tissue 32 as described herein may include any anatomy structure and/or surrounding tissue of the anatomy structure of a patient. More specifically, as shown in the illustrated embodiments of FIGS. 14-17, the anatomical object(s) 30 may include an interscalene brachial plexus (BP) 34 of the patient, which generally corresponds to the network of nerves running from the spine, formed by the anterior rami of the lower four cervical nerves and first thoracic nerve. As such, the brachial plexus 34 passes through the cervicoaxillary canal in the neck, over the first rib, and into the axilla (i.e. the armpit region), where it innervates the upper limbs and some neck and shoulder muscles. Further, the surrounding tissue 32 of the brachial plexus 34 generally corresponds to the sternocleidomastoid muscle (SM) 36, the middle scalene muscle (MCM) 38, the anterior scalene muscle (ASM) 40, and/or similar. The field of view or scene 12 of such anatomical structures is generally difficult for physicians to capture. Thus, the system and method of the present disclosure provides an improved method for detecting, locating and/or segmenting the field of view containing the BP and the surrounding tissues mentioned herein.

It should be understood, however, that the system and method of the present disclosure may be further used for any variety of medical procedures involving any anatomy structure in addition to those relating to the brachial plexus 34. For example, the anatomical object(s) 30 and the surrounding tissue 32 tissue of the upper and lower extremities, compartment blocks, etc. More specifically, in such embodiments, the anatomical object(s) 30 and the surrounding tissue 32 of the upper extremities may include interscalene muscle, supraclavicular muscle, infraclavicular muscle, and/or axillary muscle nerve blocks, which all block the brachial plexus (a bundle of nerves to the upper extremity), but at different locations. Further, the anatomical object(s) 30 and the surrounding tissue 32 of the lower extremities may include the lumbar plexus, the fascia Iliac, the femoral nerve, the sciatic nerve, the abductor canal, the popliteal, the saphenous (ankle), and/or similar. In addition, the anatomical object(s) 30 and the surrounding tissue 32 of the compartment blocks may include the intercostal space, transversus abdominus plane (TAP), and thoracic paravertebral space, and/or similar. In addition, the tissue or anatomical region to be imaged may include cardiac tissue, lung tissue, brain tissue, digestive tissue, or any other tissue or anatomical regions typically visualized by the imaging systems described above.

Further, as shown in FIGS. 14-17, the image 14 generated by the imaging system 10 or 11 may include the scene 12 as well as an optional task bar 15 located adjacent thereto. In addition, the task bar 15 may include other suitable control features such as open, start, and stop buttons as well as the date and time. It should also be understood that the image 14 may further include any other suitable control and/or display features and may be controlled via the user interface 22 or via touch-screen capabilities.

Figure 13:
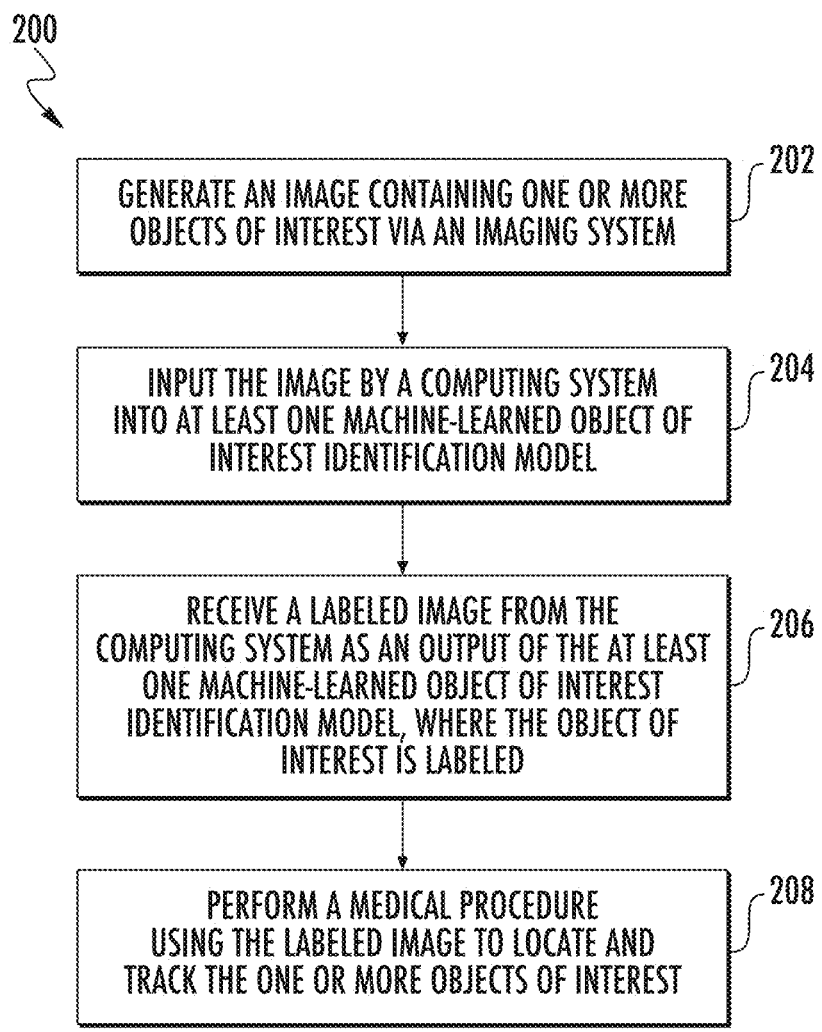
FIG. 13 illustrates a flow diagram for of a method for automatic detection, localization, and segmentation of at least one object of interest in a scene of an image generated by an imaging system according to one embodiment the present disclosure.

Referring particularly to FIG. 13, as shown at 202, the method 200 includes generating an image 14 of one or more objects of interest via the imaging system 10 or 11 and providing the entire image 14 of the one or more objects of interest (e.g., a medical instrument 145, an anatomical object 30 and/or the surrounding tissue 32). Then, as shown at step 204, the image 14 can be input, via a computing system 100, such as be utilizing a processor(s) 16 of the computing system 100, which may be a part of the imaging system 10 or 11 or may be separate from but linked to the imaging system 10 or 11, into at least one machine learned object of interest identification model 110. Further, it should be understood that the machine-learned model(s) 110 as described above are trained to automatically detect the anatomical object 30 and/or the surrounding tissue 32 in the scene 12 of the image 14. More specifically, in certain embodiments, the machine-learned model(s) 110 may include one or more deep neural networks, such as one or more convolutional neural networks (CNNs), one or more recurrent neural networks, or any other suitable neural network configurations. In machine learning, deep convolutional neural networks generally refer to a type of feed-forward artificial neural network in which the connectivity pattern between its neurons is inspired by the organization of the animal visual cortex, whose individual neurons are arranged in such a way that they respond to overlapping regions tiling the visual field. In contrast, recurrent neural networks (RNNs) generally refer to a class of artificial neural networks where connections between units form a directed cycle. Such connections create an internal state of the network which allows the network to exhibit dynamic temporal behavior. Unlike feed-forward neural networks (such as convolutional neural networks), RNNs can use their internal memory to process arbitrary sequences of inputs. As such, RNNs can extract the correlation between the image frames in order to better identify and track anatomical objects in real-time.

In certain embodiments, the processor(s) 16 may use ground truth data to train and/or develop the machine-learned model(s) 110 to automatically detect the scene 12 of the image 14 containing the medical instrument 145, an anatomical object 30 of interest, and/or the surrounding tissue 32. For example, in particular embodiments, the processor(s) 16 may be configured to initially train the machine-learned model(s) 110 to automatically detect the scene 12 containing the medical instrument 145, the anatomical object(s) 30, and/or the surrounding tissue 32. More specifically, in certain embodiments, the initial training may be completed while the processor(s) 16 is offline. In another embodiment, the processor(s) 16 may be configured to continuously train the machine-learned model(s) online to automatically detect the scene 12 containing the medical instrument 145, the anatomical object(s) of interest 30, and/or the surrounding tissue 32, e.g. after the initial training is complete.

More specifically, in particular embodiments, the processor(s) 16 may be configured for online learning to continuously train the machine-learned model(s) 110 from newly captured data in the field to automatically detect the medical instrument 145, the anatomical object of interest 30, and/or the surrounding tissue 32 in the scene 12 by scanning and collecting a dataset of images in the form of training data 162 (see FIG. 5), where the images include one or more of a medical instrument 145, an anatomical object of interest 30, and surrounding tissue 32 from multiple patients. For example, in certain embodiments, hundreds and/or thousands of images may be scanned and collected from multiple patients and stored in the dataset via the memory device(s) 18. Further, before storing, the dataset of images forming the training data 162 may be annotated (e.g., manually by a physician or other health care provider) based on user input to create the ground truth data. For example, in certain embodiments, physicians may annotate and manually identify the dataset of images based on expert knowledge to assist the machine-learned model(s) 110 in detecting and identifying the anatomical object(s) 30 and/or the surrounding tissue 32 in each image of the dataset. As such, the ground truth data as described herein generally refers to information provided by direct observation of experts in the field as opposed to information provided by inference. Thus, the machine-learned model(s) 110 of the present disclosure are configured to mimic a human brain during operation.

In particular embodiments, the dataset of images forming the training data 162 can then be divided into a plurality of groups. For example, in one embodiment, the ground truth data may be divided into at least two groups including a training dataset and a validation dataset. As such, in particular embodiments, the processor(s) 16 are configured to utilize the training dataset to train the machine-learned model(s) 110. More specifically, in certain embodiments, the processor(s) 16 may be configured to optimize a cost function to minimize an error between an output of the machine-learned model(s) 110 and the ground truth data. For example, in one embodiment, the step of optimizing the cost function to minimize the error may include utilizing a stochastic approximation, such as a stochastic gradient descent (SGD) algorithm, that iteratively processes portions of the ground truth data and adjusts one or more parameters of the machine-learned model(s) 110 based on the error between the output of the machine-learned model(s) 110 and the ground truth data. As used herein, a stochastic gradient descent generally refers to a stochastic approximation of the gradient descent optimization method for minimizing an objective function that is written as a sum of differentiable functions. More specifically, in one embodiment, the processor(s) 16 may be configured to implement supervised learning to minimize the error between the output of the machine-learned model(s) 110 and the ground truth data. As used herein, "supervised learning" generally refers to the machine learning task of inferring a function from labeled training data 162.

However, it should be understood that the cost function can be defined in different ways and can be optimized using various methods. For example, in additional embodiments, the processor(s) 16 may implement further deep learning techniques, such as reinforcement learning, unsupervised learning, and/or any other techniques now known or later developed in the art. Such methods may require less training data and/or rely on a reward/punishment function such that the systems do not need to be specifically provided with labeled data.

In another embodiment, the method 200 may also include, after optimizing the cost function, utilizing the machine-learned model(s) 110 in real-time to automatically provide predictions on the validation data as well the newly captured data. Thus, in such embodiments, the processor(s) 16 may be configured to compare the predictions with the ground truth data to ensure that the machine-learned model(s) 110 are able to generalize. In other words, the processor(s) 16 may be configured to ensure that the machine-learned model(s) 110 can provide accurate predictions for cases falling outside of the training data.

Referring still to FIG. 13, as shown at 206, the method 200 also includes receiving a labeled image from the computer system as an output of the at least one machine-learned object of interest identification model 110, where the object of interest (e.g., the medical instrument 145, the anatomical object of interest 30, and/or the surrounding tissue 32) in the scene 12 of the image 14 is annotated or labeled.

It should be understood that the machine-learned model(s) 110 can be trained to detect, locate, segment, and/or label the one or more objects of interest present in the input image(s) according to any of the suitable methods as described herein and for any particular purpose. For example, the machine-learned model(s) may first be trained to detect the medical instrument 145, the anatomical object of interest 30, and/or the surrounding tissue 32. In addition, the machine-learned model(s) 110 may also be trained to locate and segment the medical instrument 145, the anatomical object of interest 30, and/or the surrounding tissue 32. Further, in particular embodiments, differences between training the machine-learned model(s) 1110 to locate the anatomical object 30 and/or the surrounding tissue 32 versus training the machine-learned model(s) 110 to segment the medical instrument 145, the anatomical object of interest 30, and/or the surrounding tissue 32 include how the data is labeled for training and architectural details. As used herein, "segmentation" generally refers to a partition of an image into several coherent parts, but typically does not attempt to understand what such parts represent. On the other hand "semantic segmentation" generally attempts to partition the image into semantically meaningful parts, and to classify each part into one of the pre-determined classes.

Referring still to FIG. 13, as shown at 208, after a labeled image is output, displayed, or received from the processor(s) 16 of the computing system 100, the user receiving the labeled image or images can perform a medical procedure using the labeled image or images to locate and track the one or more objects of interest. For example, the user can review, in real-time, a plurality of labeled or annotated images to track the movement of a tip 146 of a medical instrument 145 that is to be used to deliver a nerve block to an anatomical object of interest 30, where the tip 146 of the medical instrument 145 is labeled for ease of visualization and tracking as the tip 146 of the medical instrument 145 is moved by the user towards the anatomical object of interest 30.

Figure 14:
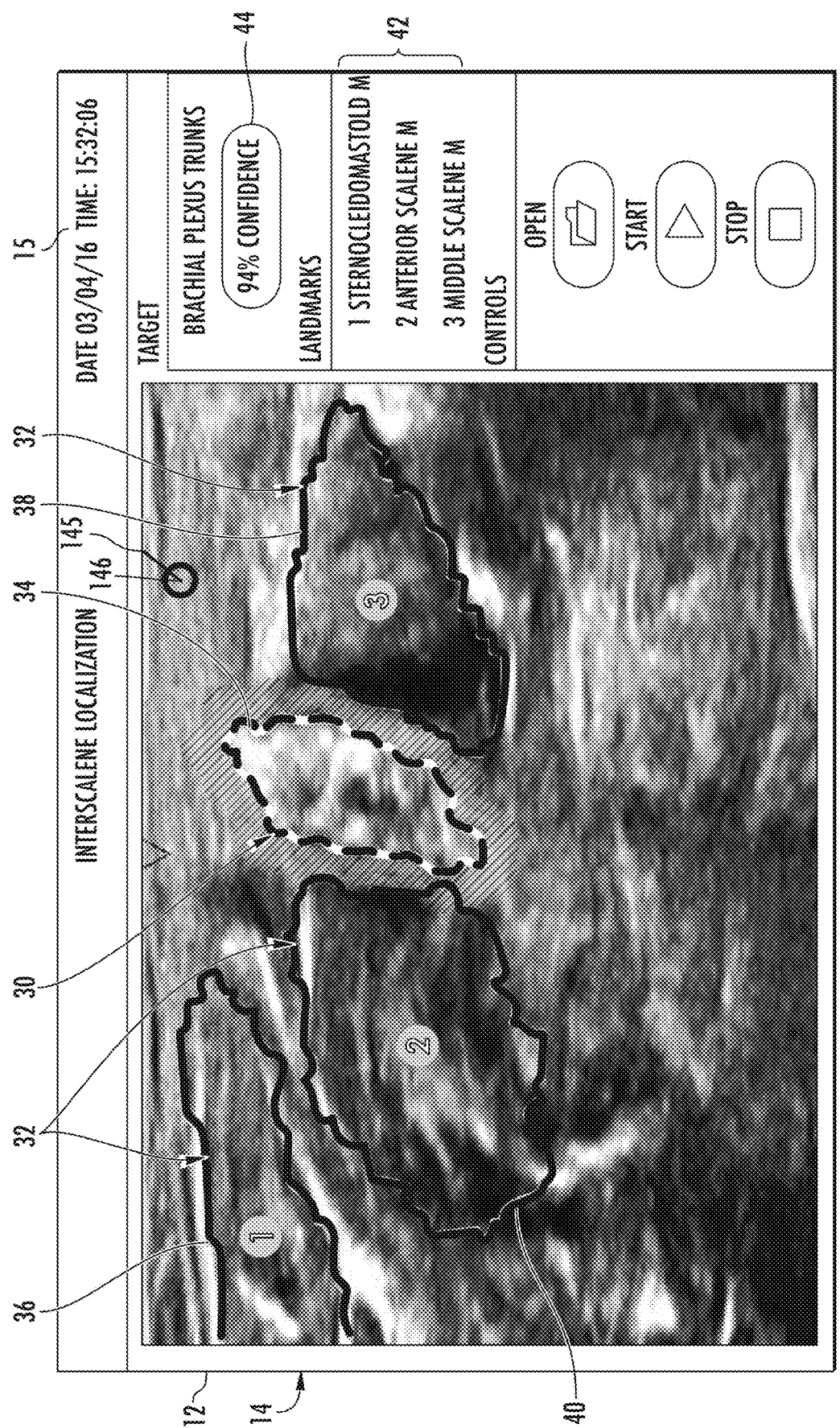
FIG. 14 illustrates a schematic diagram of one embodiment of a scene of an image generated by an imaging system according to the present disclosure, particularly illustrating both medical instrument and interscalene localization of the brachial plexus of a patient with the surrounding tissue outlined and numbered.
Figure 15:
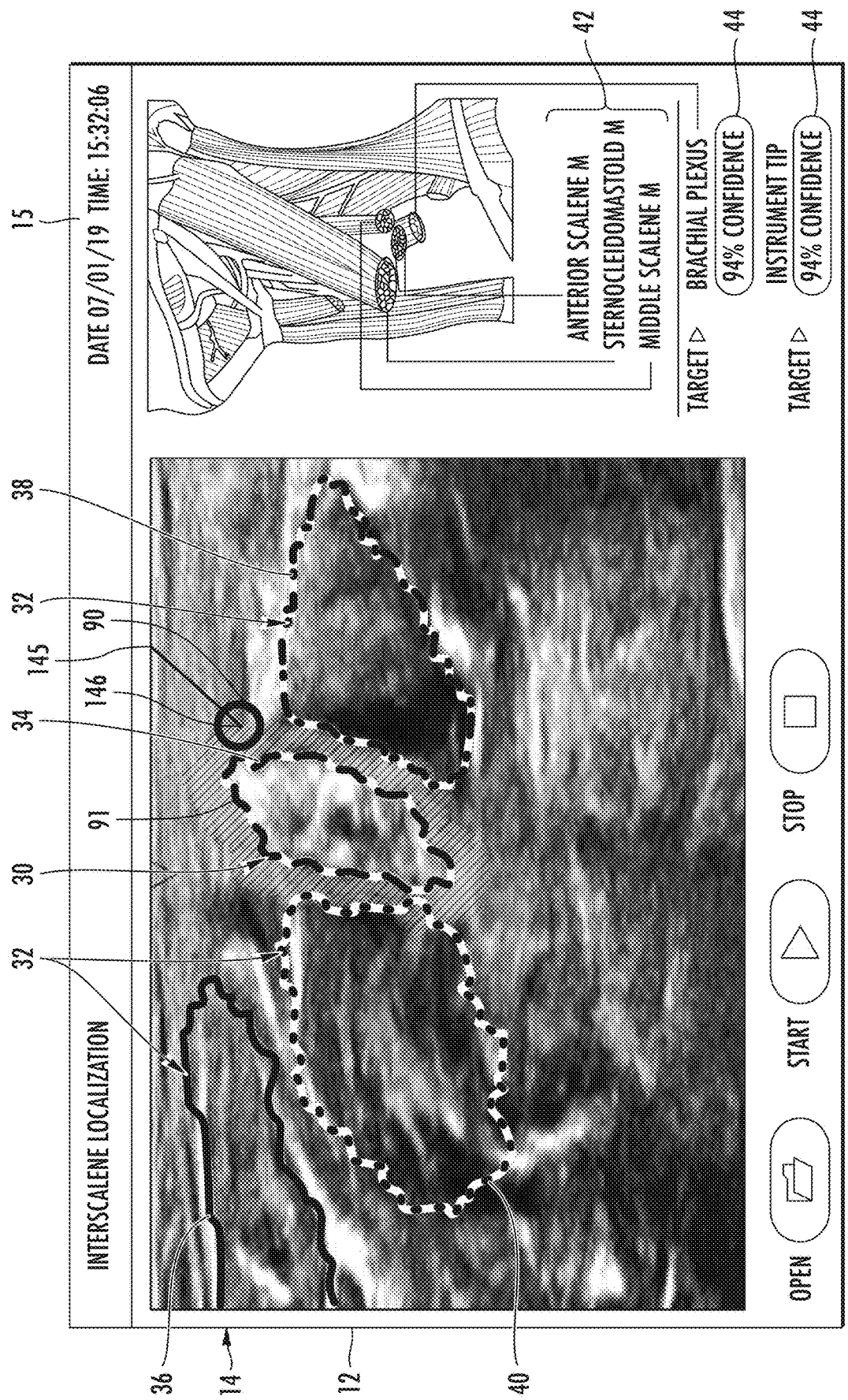
FIG. 15 illustrates a schematic diagram of another embodiment of a scene of an image generated by an imaging system according to the present disclosure, particularly illustrating both medical instrument and interscalene localization of the brachial plexus of a patient with the surrounding tissue outlined and numbered.

More specifically, in certain embodiments, the processor(s) 16 may be configured to outline the tip 146 of the medical instrument 145, the anatomical object of interest 30, and/or the surrounding tissue 32 on the image 14. For example, as shown in FIGS. 14 and 15, the tip 146 of the medical instrument 145 is outlined with a border having a first thickness or pattern, the brachial plexus 34 (i.e. the anatomical object of interest 30) is outlined with a border having a second thickness or pattern, and various surrounding tissues 32 can be outlined with a border having a third thickness that is different from the first thickness or pattern that is used to outline the tip 146 of the medical instrument 145 and that is different from the second thickness or pattern that is used to outline the brachial plexus 34. As such, a user can easily identify and distinguish the anatomical object(s) 30 of interest from the surrounding tissue 32.

Figure 16:
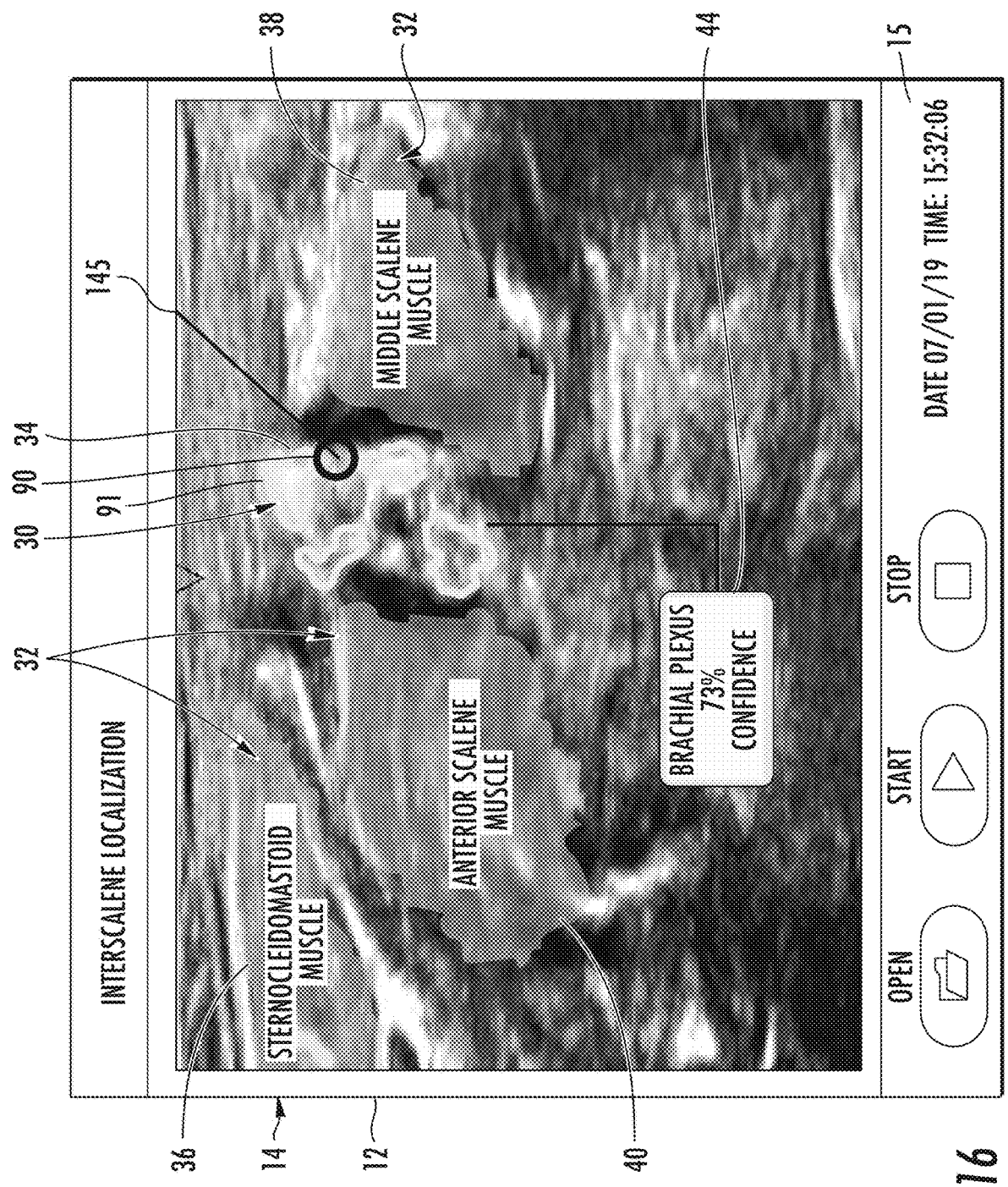
FIG. 16 illustrates a schematic diagram of yet another embodiment of a scene of an image generated by an imaging system according to the present disclosure, particularly illustrating both medical instrument and interscalene localization of the brachial plexus of a patient with the surrounding tissue shaded.
Figure 17:
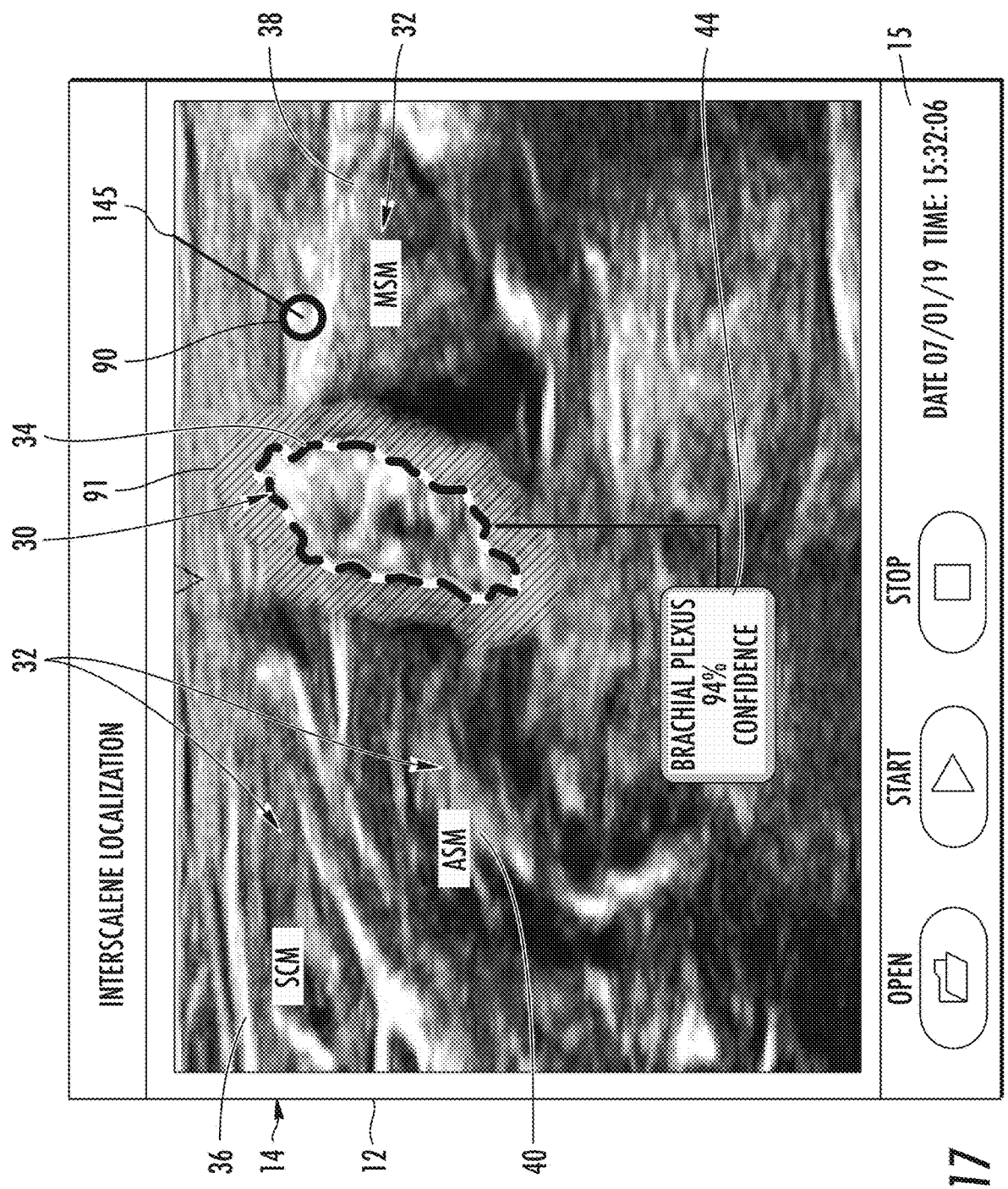
FIG. 17 illustrates a schematic diagram of one embodiment of a scene of an image generated by an imaging system according to the present disclosure, particularly illustrating both medical instrument and interscalene localization of the brachial plexus of a patient.

In further embodiments, the processor(s) 16 may be configured to overlay a descriptive label atop the medical instrument 145, the anatomical object of interest 30, and/or surrounding tissue 32 on the image 14. For example, as shown in FIG. 14, the surrounding tissue 32 may be numbered and labeled as landmarks 42 (e.g., on the right side of the image 14) with a numerical legend for easy identification via a physician. Alternatively, as shown in FIG. 15, the medical instrument 145, the anatomical object of interest 30 (e.g., the brachial plexus in FIG. 15), and the surrounding tissue 32 may be identified and distinguished by line type and identified as landmarks 42 or via an illustration particularly showing a location within the body of the patient. In still another embodiment, as shown in FIG. 16, the surrounding tissue 32 may be shaded and labeled using a descriptive medical name. In further embodiments, as shown in FIGS. 16-17, the anatomical object of interest 30 may also be further defined and/or segmented. As such, in the case of the brachial plexus 34, a user can easily identify separate nerves or nerve bundles during a nerve block procedure, when precise placement of the tip 146 of the medical instrument 145 may be critical.

In additional embodiments, and referring to FIGS. 14-17, the processor(s) 16 may also be configured to determine a confidence level 44 of the precise identification of the tip 146 of medical instrument 145, the anatomical object of interest 30, and/or the surrounding tissue 32. For example, as shown in FIG. 15, the confidence level 44 of the location of the brachial plexus and/or the tip 146 of the medical instrument 145 is located on the task bar of the image 14. Alternatively, as shown in FIGS. 16 and 17 the confidence level 44 of the location of the brachial plexus and/or the tip 146 of medical instrument 145 (not shown) may be located within the scene 12 of the image 14, e.g. adjacent to the anatomical object of interest 30 and or the tip 146 of the medical instrument 145.

Figure 18:
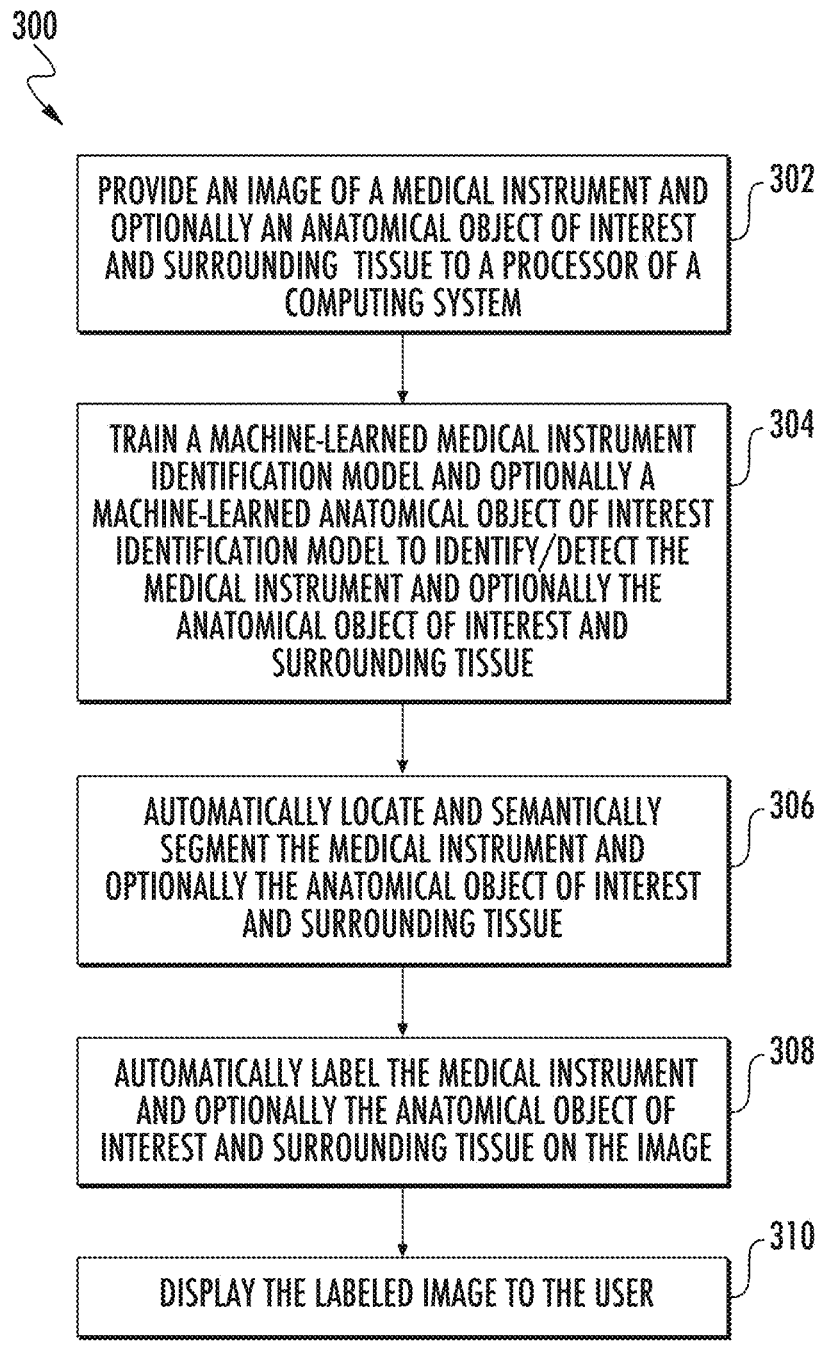
FIG. 18 illustrates a flow diagram for a method for automatic detection, localization, and segmentation of at least one object of interest in a scene of an image generated by an imaging system according to the present disclosure.
Figure 19:
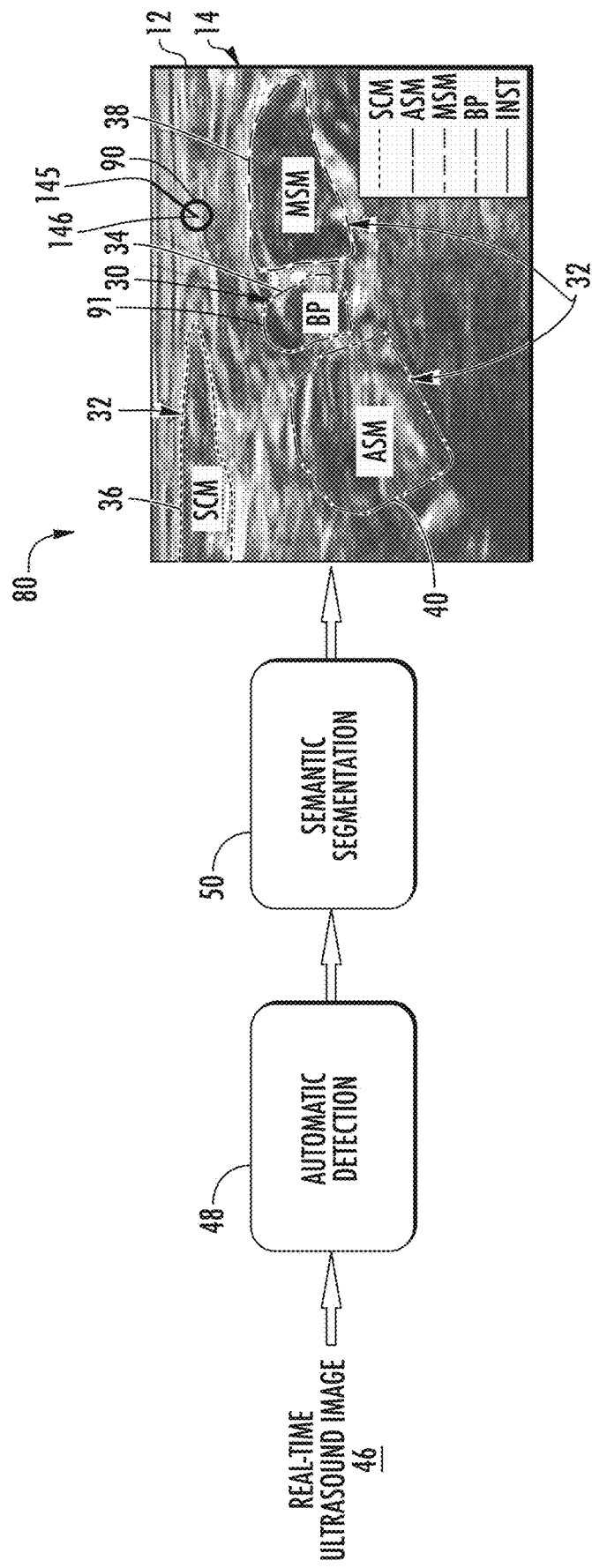
FIG. 19 illustrates a flow diagram of a method for automatic detection, localization, and segmentation of at least one object of interest in a scene of an image generated by an imaging system according to the present disclosure, particularly illustrating interscalene localization of the brachial plexus of a patient with the surrounding tissue labeled.

Referring now to FIGS. 18 and 19, a schematic diagram and a flow diagram of another embodiment of a method 300 for the automatic identification/detection, localization, and semantic segmentation of a medical instrument and optionally an anatomical object of interest in a scene of an image generated by an imaging system are illustrated. As shown at 302 of FIG. 18, the method 300 includes providing an image 46 or 70 of a medical instrument 145 and optionally an anatomical object of interest 30 to a processor 16 of a computing system 100. For example, as shown in FIG. 19, a real-time ultrasound image 46 may be provided to the processor 16. As shown at 304 of FIG. 18, the method 300 further includes training a machine-learned medical instrument identification model 110a and optionally a machine-learned anatomical object of interest identification model 110b to identify or detect the medical instrument 145 and optionally the anatomical object of interest 30 contained within the ultrasound image 46 or 70. For example, as shown in FIG. 19, the processor 16 is configured to receive the real-time ultrasound image 46 and automatically detect the medical instrument 145 and optionally the anatomical object of interest 30, and even the surrounding tissue 32 in the scene 12 at block 48. As shown at 306 of FIG. 18, the method 300 then includes automatically locating and semantically segmenting the medical instrument 145, and optionally the anatomical object of interest 30 and the surrounding tissue 32 in the scene 12. For example, as shown in FIG. 19, the processor 16 is configured to implement semantic segmentation at block 50. Then, as shown at 308 of FIG. 18, the method 300 includes automatically labeling, via the processor 16, the tip 146 of the medical instrument 145 and optionally the anatomical object of interest 30 and surrounding tissue 32 on the image 80. As shown at 310 of FIG. 18, the method 300 includes displaying the labeled image to a user. For example, as shown in FIG. 19, the processor 16 is configured to display the labeled image 80 via the user display 20.

Figure 20:
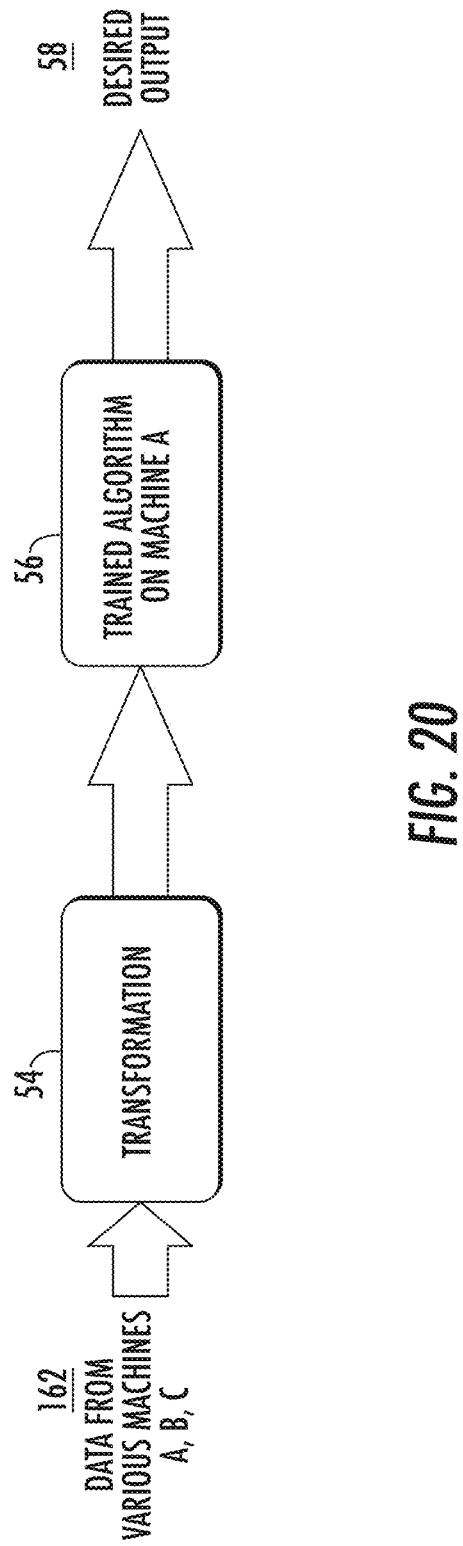
FIG. 20 illustrates a schematic diagram of a method for pre-processing an image generated by an imaging system according to the present disclosure.

Turning now to FIG. 20, the present disclosure contemplates that, in some embodiments, the real-time ultrasound image 46 or 70 that is provided to the processor 16 may be obtained from one imaging system (e.g., a first ultrasound machine A), while the dataset of images forming the training data 162 used to create the ground truth data for developing and training the deep learning network may be collected from various machines, such as the first ultrasound machine A, a second ultrasound machine B, a third ultrasound machine C, and etc. Thus, because the dataset of images used to create the ground truth data can include images captured from different imaging systems, the images in the dataset can vary significantly in terms of various characteristics including image size, intensity, contrast, texture, etc. These variances can pose limitations on the use of a machine-learned model across different imaging system. Thus, FIG. 20 illustrates a schematic diagram of a method for pre-processing images generated by one or more imaging systems so that the images are consistent across, for instance, multiple ultrasound imaging systems, such as machines A, B, and C. Generally, the training data 162 from machines A, B, and C (e.g., the dataset of images forming the training data 162) can be transformed (or pre-processed) at block 54, after which the training data 162, which is now more consistent across the various machines A, B, and C, is used to create a trained algorithm at block 56 to achieve the desired output 58 despite obtaining the dataset of images for the training data 162 from multiple ultrasound imaging systems.

More specifically, the typical process in developing a machine-learned model includes collecting data from an imaging system (e.g., an ultrasound imaging machine), cleaning the images, annotating the images, and then using the images and annotations for developing learning-based algorithms as generally described above. However, one of the main challenges with the use of such algorithms is the aforementioned variability amongst different imaging systems, where captured images can vary in terms of image size, intensity, contrast, texture, etc. As such, the machine-learned model that is trained using a particular imaging system can face difficulty in processing and inferring the desired output data and images captured from other imaging systems. The present disclosure overcomes this challenge by performing a pre-processing step on the data 52 coming from multiple different machines to transform the image dataset at block 54 into a consistent set of data that has been transformed so that the deep learning network can be trained more precisely and accurately at block 56, resulting in the desired output 58 (e.g., a robust deep learning networking). The pre-processing step or transformation at block 54 includes resizing images in the dataset into a fixed, consistent size and then applying imaging normalization techniques such as image histogram equalization and image histogram matching to improve the consistency between the various images, resulting in a set of equalized images obtained by adjusting the original image based on histogram equalization. Thus, the dataset input into the machine-learned model 110 in the form of training data 162 can have similar statistical features that will ensure the desired output 58 across different imaging systems. As a result of the transformation step, the dataset can be converted into a consistent dataset for the deep-learning algorithm.

It should be understood that as used herein, the term "histogram" refers to a graphical representation showing a visual impression of the distribution of data. An image histogram is a specific type of histogram that acts as a graphical representation of the lightness/color distribution in a digital image, where the image histogram plots the number of pixels for each value. Further, as used herein, the term "histogram equalization" refers to a method in image processing of contrast adjustment using an image's histogram. The method usually increases the global contrast of many images, especially when the usable data of the image is represented by close contrast values. Through this adjustment, the intensities can be better distributed on the histogram. This allows for areas of lower local contrast to gain a higher contrast. Histogram equalization accomplishes this by effectively spreading out the most frequent intensity values. In addition, as used herein, the term "histogram matching" or "histogram specification" refers to the transformation of an image so that its histogram matches a specified histogram. This well-known histogram equalization method is a special case in which the specified histogram is uniformly distributed. Histogram matching can be used to normalize two images, such as when the images were acquired with different medical imaging devices. In this manner, the deep learning network utilized in the method for automatic detection, localization, and segmentation of an anatomical object that is contemplated by the present disclosure can be machine agnostic.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for labeling a medical instrument in at least one image generated by at least one imaging system, the method comprising:

obtaining, by a computing system comprising one or more computing devices, patient imaging data including the at least one image from the at least one imaging system;

inputting, by the computing system, the patient imaging data into a machine-learned medical instrument identification model;

inputting, by the computing system, the patient imaging data into a machine-learned anatomical object of interest identification model;

receiving, by the computing system as an output of the machine-learned medical instrument identification model, a first label on the at least one image corresponding with a predicted location of a tip of the medical instrument, wherein at least a portion of the medical instrument is labeled via the first label, wherein the first label identifies a tip of the medical instrument, wherein the first label comprises an outline of the tip of the medical instrument;

receiving, by the computing system as an output of the machine-learned anatomical object of interest identification model, a second label on the at least one image corresponding with a predicted location of at least a portion of an anatomical object of interest, wherein at least a portion of the anatomical object of interest is labeled via the second label, wherein the first label and the second label are overlaid onto the at least one image in real-time;

determining, by the computing system and via an objective function, a confidence level in relation to each of the predicted location of the tip of the medical instrument and the predicted location of at least a portion of the anatomical object of interest; and displaying, by the computing system, the labeled image concurrently with an indication of at least one of the determined confidence levels.

2. The method of claim 1, wherein the machine-learned medical instrument identification model comprises one or more of a convolutional neural network and a recurrent neural network.

3. The method of claim 1, wherein the machine-learned anatomical object of interest identification model comprises one or more of a convolutional neural network and a recurrent neural network.

4. The method of claim 1, wherein the first label is visually distinguishable from the second label.

5. The method of claim 1, wherein the at least one imaging system comprises one or more of an ultrasound imaging system, a computer tomography scanner, and a magnetic resonance imaging scanner.

6. The method of claim 1, wherein the computing system is separate from the at least one imaging system.

7. The method of claim 1, wherein the computing system is a part of the at least one imaging system.

8. A computing system, comprising:
a machine-learned medical instrument identification model trained to label at least a portion of a medical instrument based on patient imaging data containing at least one image received from at least one imaging system;
a machine-learned anatomical object of interest identification model trained to label at least a portion of an anatomical object of interest based on the patient imaging data containing the at least one image;
one or more processors;
one or more non-transitory computer-readable media that store instructions that, when executed by the one or more processors, cause the one or more processors to perform operations, the operations comprising:
obtaining the patient imaging data containing the at least one image;
inputting the patient imaging data containing the at least one image into the machine-learned medical instrument identification model; and
receiving, as an output of the machine-learned medical instrument identification model, a first label on the image corresponding with a predicted location of a tip of the medical instrument, wherein at least a portion of the medical instrument is labeled via the first label, wherein the first label identifies a tip of the medical instrument, wherein the first label comprises an outline of the tip of the medical instrument;
inputting the patient imaging data containing the at least one image into the machine-learned anatomical object of interest identification model; and
receiving, as an output of the machine-learned anatomical object of interest identification model, a second label on the image corresponding with a predicted location of at least a portion of the anatomical object of interest, wherein at least a portion of the anatomical object of interest is labeled via the second label, wherein the first label and the second label are overlaid onto the at least one image in real-time;
determining, via an objective function, a confidence level in relation to each of the predicted location of the tip of the medical instrument and the predicted location of at least a portion of the anatomical object of interest; and
a display configured to display the labeled image to a user concurrently with an indication of at least one of the determined confidence levels.

9. The computing system of claim 8, wherein the machine-learned medical instrument identification model comprises one or more of a convolutional neural network and a recurrent neural network.

10. The computing system of claim 8, wherein the machine-learned anatomical object of interest identification model comprises one or more of a convolutional neural network and a recurrent neural network.

11. The computing system of claim 8, wherein the first label is visually distinguishable from the second label.

12. The computing system of claim 8, wherein the computing system is a part of the at least one imaging system.

13. The computing system of claim 12, wherein the at least one imaging system comprises one or more of an ultrasound imaging system, a computer tomography scanner, and a magnetic resonance imaging scanner.

* * * * *